US012023067B2

(12) United States Patent
Scott

(10) Patent No.: US 12,023,067 B2
(45) Date of Patent: *Jul. 2, 2024

(54) BALANCING FEATURE FOR REUSABLE TROCAR

(71) Applicant: Cilag GmbH International, Zug (CH)

(72) Inventor: Gregory G. Scott, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 0 days.

This patent is subject to a terminal disclaimer.

(21) Appl. No.: 18/077,326

(22) Filed: Dec. 8, 2022

(65) Prior Publication Data
US 2023/0225759 A1    Jul. 20, 2023

Related U.S. Application Data

(63) Continuation of application No. 17/213,437, filed on Mar. 26, 2021, now Pat. No. 11,559,329.

(Continued)

(51) Int. Cl.
*A61B 17/34*    (2006.01)
*A61M 13/00*    (2006.01)

(52) U.S. Cl.
CPC ...... *A61B 17/3423* (2013.01); *A61B 17/3415* (2013.01); *A61B 2017/3454* (2013.01); *A61B 2017/3488* (2013.01); *A61M 13/003* (2013.01)

(58) Field of Classification Search
CPC ............ A61B 17/3423; A61B 17/3415; A61B 2017/3454; A61B 2017/3488;

(Continued)

(56) References Cited

U.S. PATENT DOCUMENTS 4,699,616 A    10/1987 Nowak et al.
5,147,316 A    9/1992 Castillenti
(Continued)

FOREIGN PATENT DOCUMENTS

AU    702882 B2    3/1993
CN    106344126 B    2/2019
(Continued)

OTHER PUBLICATIONS

International Search Report and Written Opinion dated Jul. 22, 2021, for International Application No. PCT/EP2021/061421, 15 pages.

(Continued)

*Primary Examiner* — Tracy L Kamikawa
(74) *Attorney, Agent, or Firm* — Frost Brown Todd LLP

(57) ABSTRACT

A surgical access device assembly includes a cannula hub and a cannula tube. The cannula tube extends distally from the cannula hub along a longitudinal axis. The cannula tube defines a working channel. The cannula tube includes a tissue engagement feature and a balancing feature. The balancing feature is configured to promote lateral stability of the cannula tube and the cannula hub relative to the body cavity wall of the patient. The balancing feature includes a proximal portion of the cannula tube having a first wall thickness. The balancing feature also includes a distal portion of the cannula tube having a second wall thickness that is greater than the first wall thickness. At least a portion of the proximal portion is proximal relative to the tissue engagement feature. At least a portion of the distal portion is distal relative to the tissue engagement feature.

19 Claims, 16 Drawing Sheets

Related U.S. Application Data

(60) Provisional application No. 63/018,558, filed on May 1, 2020.

(58) Field of Classification Search
CPC .... A61B 2017/3433; A61B 2017/3458; A61B 2017/3482
See application file for complete search history.

(56) References Cited

U.S. PATENT DOCUMENTS

| | | | |
|---|---|---|---|
| 5,215,531 A | 6/1993 | Maxson et al. | |
| 5,256,147 A | 10/1993 | Vidal et al. | |
| 5,263,939 A | 11/1993 | Wortrich | |
| 5,267,970 A | 12/1993 | Chin et al. | |
| 5,364,372 A | 11/1994 | Danks et al. | |
| 5,792,135 A | 8/1998 | Madhani et al. | |
| 5,800,451 A | 9/1998 | Buess et al. | |
| 5,817,061 A | 10/1998 | Goodwin et al. | |
| 5,833,666 A | 11/1998 | Davis et al. | |
| 6,620,173 B2 | 9/2003 | Gerbi et al. | |
| 6,638,265 B1 | 10/2003 | Ternamian | |
| 7,473,220 B2 | 1/2009 | Francese et al. | |
| 7,503,893 B2 | 3/2009 | Kucklick | |
| 7,614,401 B2 | 11/2009 | Thompson | |
| 7,874,982 B2 * | 1/2011 | Selover | A61B 17/3421 600/199 |
| 7,981,092 B2 | 7/2011 | Duke | |
| 8,162,893 B2 | 4/2012 | Okihisa et al. | |
| 8,226,553 B2 | 7/2012 | Shelton, IV et al. | |
| 8,251,900 B2 | 8/2012 | Ortiz et al. | |
| 8,435,174 B2 * | 5/2013 | Cropper | A61B 17/3421 600/203 |
| 8,479,969 B2 | 7/2013 | Shelton, IV | |
| 8,491,533 B2 | 7/2013 | Parihar et al. | |
| 8,551,049 B2 | 10/2013 | Ott et al. | |
| 8,551,050 B2 | 10/2013 | Ott et al. | |
| 8,568,362 B2 | 10/2013 | Moreno, Jr. et al. | |
| 8,573,465 B2 | 11/2013 | Shelton, IV | |
| 8,579,807 B2 | 11/2013 | Moreno, Jr. et al. | |
| 8,608,715 B2 | 12/2013 | Roberts et al. | |
| 8,636,686 B2 | 1/2014 | Minnelli et al. | |
| 8,690,831 B2 | 4/2014 | Duke | |
| 8,783,541 B2 | 7/2014 | Shelton, IV et al. | |
| 8,800,838 B2 | 8/2014 | Shelton, IV | |
| 8,821,527 B2 * | 9/2014 | Farnan | A61M 60/221 606/190 |
| 8,870,749 B2 | 10/2014 | Fouts et al. | |
| 9,101,315 B2 | 8/2015 | Winfree et al. | |
| 9,113,951 B2 | 8/2015 | Richard et al. | |
| 9,289,200 B2 | 3/2016 | Dang et al. | |
| 9,675,379 B2 | 3/2017 | Kucklick | |
| 9,668,723 B2 | 6/2017 | Keating et al. | |
| 10,327,809 B2 | 6/2019 | Buyda et al. | |
| 10,368,907 B2 | 8/2019 | Ravikumar et al. | |
| 10,426,873 B2 | 10/2019 | Schultz | |
| 10,617,444 B2 | 4/2020 | Kellner et al. | |
| 10,792,069 B2 | 10/2020 | Hall et al. | |
| 10,820,924 B2 | 11/2020 | Hall et al. | |
| 10,874,426 B2 | 12/2020 | Holsten et al. | |
| 11,013,531 B2 | 5/2021 | McIntyre et al. | |
| 11,051,845 B2 | 7/2021 | Lee | |
| 11,109,890 B2 | 9/2021 | Druma et al. | |
| 11,389,192 B2 | 7/2022 | Shelton, IV et al. | |
| 11,559,329 B2 * | 1/2023 | Scott | A61B 17/3415 |
| 11,607,507 B2 | 3/2023 | Geisz et al. | |
| 11,633,211 B2 | 4/2023 | Muthuchidambaram et al. | |
| 11,712,267 B2 | 8/2023 | McLain | |
| 2010/0010449 A1 | 1/2010 | Leibowitz et al. | |
| 2013/0116510 A1 | 5/2013 | Lutze et al. | |
| 2014/0371763 A1 | 12/2014 | Poll et al. | |
| 2015/0087913 A1 * | 3/2015 | Dang | A61B 17/3423 600/204 |
| 2017/0245889 A1 | 8/2017 | Herrell et al. | |
| 2019/0000496 A1 * | 1/2019 | Shelton, IV | A61B 17/3417 |
| 2019/0343552 A1 * | 11/2019 | Yaffe | A61B 17/3474 |
| 2021/0338269 A1 | 11/2021 | Scott et al. | |
| 2021/0338273 A1 | 11/2021 | Vijayachandran et al. | |
| 2021/0338274 A1 | 11/2021 | Scott et al. | |
| 2021/0338275 A1 | 11/2021 | Vijayachandran | |
| 2021/0338278 A1 | 11/2021 | Scott et al. | |
| 2021/0338281 A1 | 11/2021 | Mozloom, Jr. et al. | |
| 2021/0338282 A1 | 11/2021 | Vijayachandran et al. | |
| 2021/0338371 A1 | 11/2021 | Harris et al. | |
| 2023/0082376 A1 | 3/2023 | Warber et al. | |

FOREIGN PATENT DOCUMENTS

| | | |
|---|---|---|
| DE | 202007001745 U1 | 4/2007 |
| EP | 1884210 A2 | 2/2008 |
| EP | 2174602 A1 | 4/2010 |
| KR | 2016 0017996 A | 2/2016 |
| WO | WO 1999/052457 A1 | 10/1999 |
| WO | WO 2012/128826 A2 | 9/2012 |
| WO | WO 2013/012368 A1 | 1/2013 |
| WO | WO 2014/137530 A1 | 9/2014 |
| WO | WO 2015/049391 A1 | 4/2015 |
| WO | WO 2017/132004 A1 | 8/2017 |
| WO | WO 2018/013734 A1 | 1/2018 |
| WO | WO 2020/036497 A1 | 2/2020 |
| WO | WO 2020/036498 A1 | 2/2020 |
| WO | WO 2020/040649 A1 | 2/2020 |

OTHER PUBLICATIONS

International Search Report and Written Opinion dated Aug. 3, 2021, for International Application No. PCT/EP2021/061428, 15 pages.

International Search Report and Written Opinion dated Jul. 16, 2021, for International Application No. PCT/EP2021/061442, 13 pages.

International Search Report and Written Opinion dated Jul. 8, 2021, for International Application No. PCT/EP2021/061447, 15 pages.

International Search Report and Written Opinion dated Jul. 27, 2021, for International Application No. PCT/EP2021/061456, 14 pages.

International Search Report and Written Opinion dated Jul. 13, 2021, for International Application No. PCT/EP2021/061459, 16 pages.

International Search Report and Written Opinion dated Jul. 20, 2021, for International Application No. PCT/EP2021/061466, 17 pages.

International Search Report and Written Opinion dated Jul. 15, 2021, for International Application No. PCT/EP2021/061468, 16 pages.

International Search Report and Written Opinion dated Aug. 3, 2021, for International Application No. PCT/EP2021/061437, 17 pages.

International Search Report and Written Opinion dated Aug. 3, 2021, for International Application No. PCT/EP2021/061460, 12 pages.

* cited by examiner

BALANCING FEATURE FOR REUSABLE TROCAR

PRIORITY

This Application is a continuation of U.S. patent application Ser. No. 17/213,437, entitled "Balancing Feature for Reusable Trocar," filed on Mar. 26, 2021, issued as U.S. Pat. No. 11,559,329 on Jan. 24, 2023; which claims priority to U.S. Provisional Pat. App. No. 63/018,558, entitled "Balancing Feature for Reusable Trocar," filed on May 1, 2020.

BACKGROUND

Some surgical procedures may require a clinician to access a surgical site via the abdominal cavity of a patient. To gain such access, an opening is first formed through the abdominal wall tissue overlying the abdominal cavity. In some surgical procedures (referred to as "laparoscopic" or "endoscopic" surgeries), a relatively small opening is made through the abdominal wall tissue, and the surgical site is then accessed with elongate instruments inserted through an access device generally referred to as a "trocar" positioned within the opening. Traditional trocars generally include a cannula assembly and an obturator that is removably received within a working channel of the cannula assembly. In use, the obturator is mated with the cannula assembly, and the combined structure (i.e., the trocar) is directed by a clinician downwardly through the abdominal wall of the patient such that the distal ends of the obturator and the cannula assembly extend into the abdominal cavity. The clinician then withdraws the obturator from the cannula assembly so that surgical instruments may be directed downwardly through the working channel of the cannula assembly to access the surgical site.

Merely exemplary versions of trocars, components thereof, and other varieties of surgical access devices are disclosed in U.S. Pat. No. 7,981,092, entitled "Vibratory Trocar," issued Jul. 19, 2011; U.S. Pat. No. 8,226,553, entitled "Access Device with Insert," issued on Jul. 24, 2012; U.S. Pat. No. 8,251,900, entitled "Surgical Access Devices and Methods Providing Seal Movement in Predefined Paths," issued on Aug. 28, 2012; U.S. Pat. No. 8,579,807, entitled "Absorbing Fluids in a Surgical Access Device," issued on Nov. 12, 2013; U.S. Pat. No. 8,568,362, entitled "Surgical Access Device with Sorbents," issued on Oct. 29, 2013; U.S. Pat. No. 8,636,686, entitled "Surgical Access Device," issued on Jan. 28, 2014; U.S. Pat. No. 8,690,831, entitled "Gas Jet Fluid Removal in a Trocar," issued on Apr. 8, 2014; and U.S. Pat. Pub. No. 2019/0000496, entitled "Method of Suturing a Trocar Path Incision," published Jan. 3, 2019, issued as U.S. Pat. No. 11,389,192 on Jul. 19, 2022. The disclosure of each of the above-cited U.S. Patents and Publications is incorporated by reference herein.

While various kinds of surgical instruments, including surgical access devices and end effectors, and other associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

Figure 1:
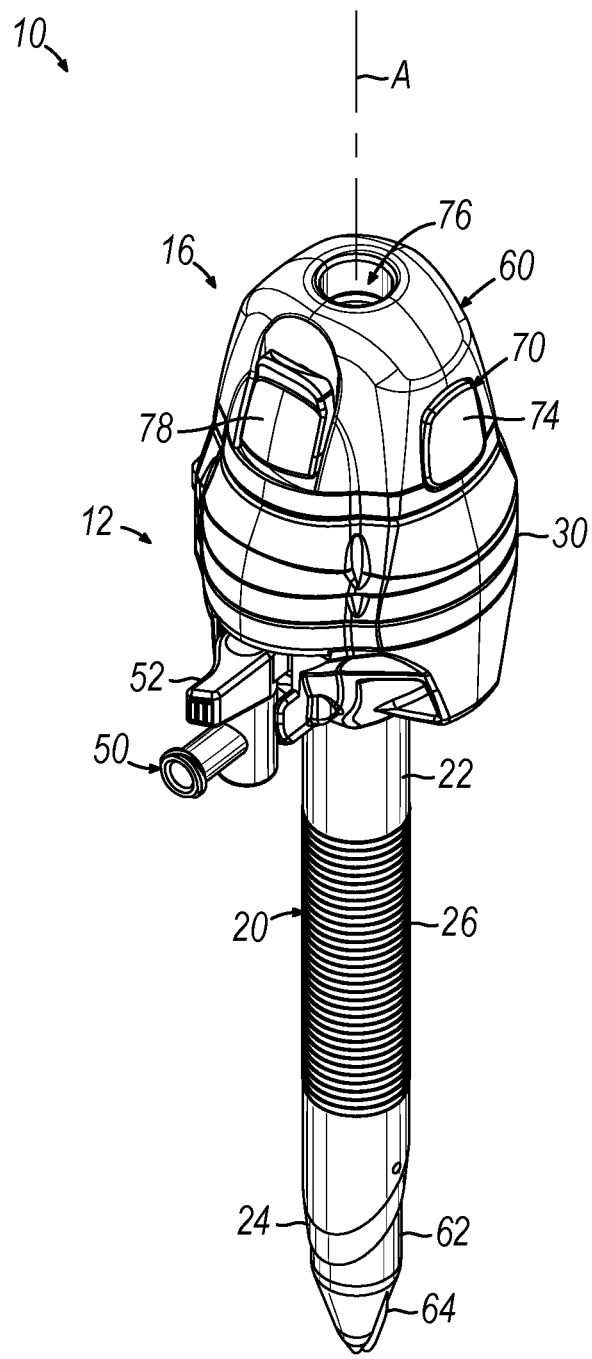
FIG. 1 depicts a perspective view of an exemplary trocar having a cannula assembly and an obturator shown in an assembled state.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

For clarity of disclosure, the terms "proximal" and "distal" are defined herein relative to a surgeon, or other operator, grasping a surgical device. The term "proximal" refers to the position of an element arranged closer to the surgeon, and the term "distal" refers to the position of an element arranged further away from the surgeon. Moreover, to the extent that spatial terms such as "top," "bottom," "upper," "lower," "vertical," "horizontal," or the like are used herein with reference to the drawings, it will be appreciated that such terms are used for exemplary description purposes only and are not intended to be limiting or absolute. In that regard, it will be understood that surgical instruments such as those disclosed herein may be used in a variety of orientations and positions not limited to those shown and described herein.

Furthermore, the terms "about," "approximately," and the like as used herein in connection with any numerical values or ranges of values are intended to encompass the exact value(s) referenced as well as a suitable tolerance that enables the referenced feature or combination of features to function for the intended purpose(s) described herein.

I. Exemplary Single-Use and Reusable Trocars

FIGS. 1-5 depict exemplary surgical access devices in the form of a single-use first trocar (10) and a reusable second trocar (110), each configured to provide surgical site access in a laparoscopic surgical procedure. Each trocar (10, 110) includes a cannula assembly (12, 112) having a working channel (14, 114), and an obturator (16, 116) configured to be removably inserted coaxially into the working channel (14, 114) so that the assembled trocar (10, 110) may be directed distally through the abdominal wall of a patient and into the abdominal cavity, for example as described below in connection with FIGS. 3A-3D.

A. Exemplary Single-Use Trocar

Figure 2:
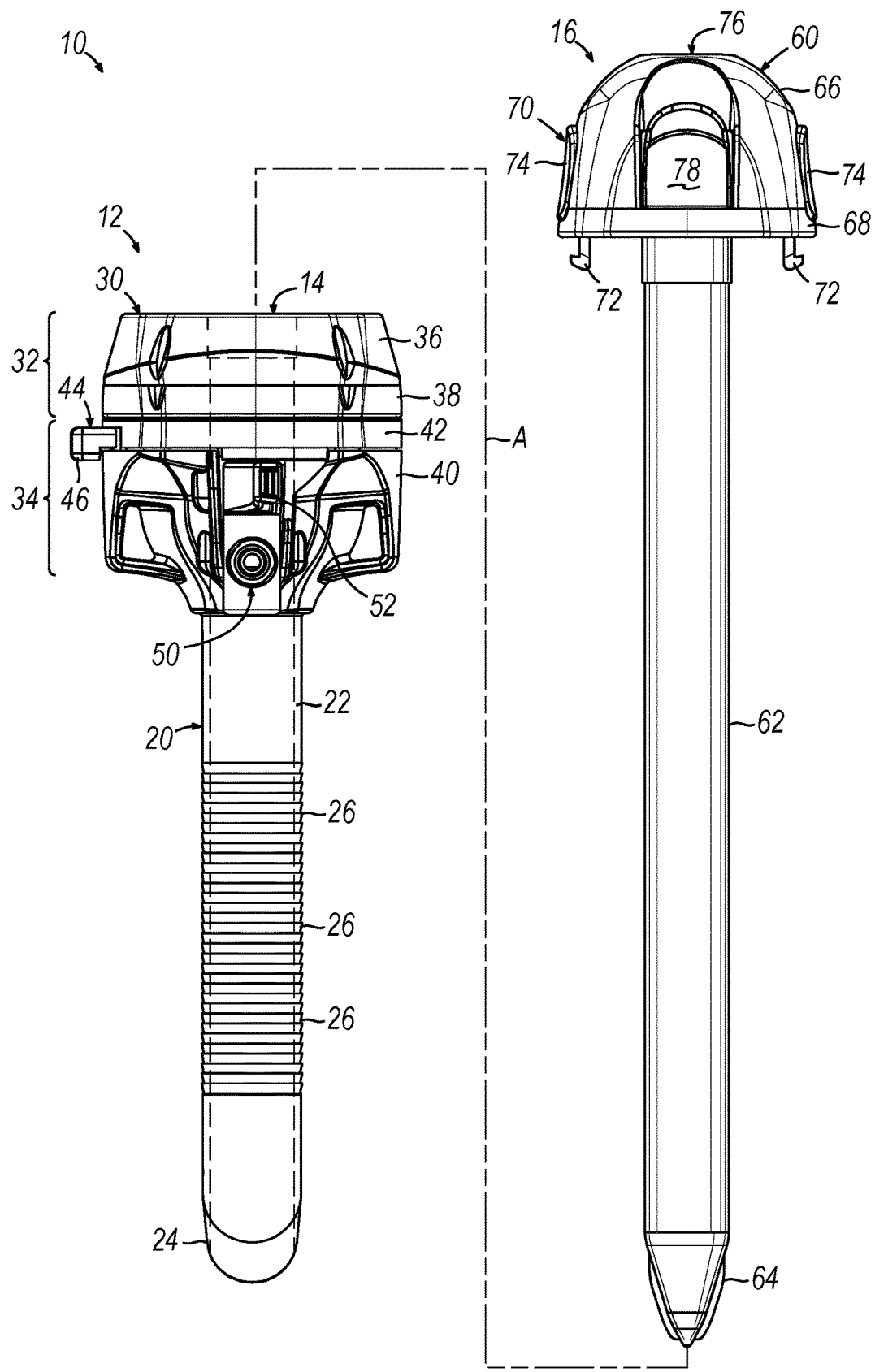
FIG. 2 depicts a side elevational view of the cannula assembly and the obturator of FIG. 1 in a disassembled state.

As shown in FIGS. 1-2, cannula assembly (12) of single-use trocar (10) includes a cannula (20) and a seal housing (30). Cannula (20) and seal housing (30) cooperate to define working channel (14), which extends longitudinally along a central axis (A) of trocar (10). In particular, working channel (14) is defined by a lumen of cannula (20) in communication with a hollow interior of seal housing (30). Cannula assembly (12) is configured to receive elongate surgical instruments distally through working channel (14) to provide access to surgical sites within the abdominal cavity of a patient. As described in greater detail below, seal housing (30) houses a pair of seal structures defining a seal assembly configured to maintain insufflation of the patient's abdominal cavity while permitting passage of surgical instruments and tissue fragments along working channel (14).

Cannula (20) of the present version may include a bell-shaped hub (not shown) at a proximal end thereof, and an elongate cylindrical tube (22) extending distally from the hub and terminating at an angled cannula tip (24). An outer surface of cannula tube (22) includes a plurality of tissue gripping features in the form of annular ribs (26) arranged axially along a medial portion of cannula tube (22). Ribs (26) are configured to grip the layers of abdominal wall tissue through which cannula (20) is inserted, and thereby assist in stabilizing cannula (20) in axial and radial directions while cannula (20) is positioned within the opening formed in the abdominal wall of a patient.

More specifically, tissue gripping ribs (26) of the present example are formed as annular scallops in the sidewall of cannula tube (22) such that each rib (26) tapers radially inwardly in a distal direction from a radially outermost edge of the rib (26). The radially outermost edges of ribs (26) are thus generally flush with the non-ribbed proximal and distal portions of cannula tube (22). The resulting configuration of ribs (26) promotes advancement of cannula tube (22) through tissue layers in a distal direction and resists retraction of cannula tube (22) through the tissue layers in a reverse, proximal direction. Advantageously, this configuration protects against unintended withdrawal of cannula tube (22) from the abdominal wall of patient during a surgical procedure. It will be appreciated, however, that cannula tube (22) may be provided with various other types of tissue gripping features in other versions of trocar (10). For instance, cannula tube (22) may include a tissue gripping feature in the form of one or more helical ribs that extend around at least a medial portion of cannula tube (22), and which may be scalloped similar to ribs (26).

Seal housing (30) of cannula assembly (12) includes a proximal housing portion (32) and a distal housing portion (34) to which proximal housing portion (32) is removably attached. Proximal housing portion (32) includes a proximal head (36) and a distal base (38) secured together. Distal housing portion (34) includes a distal shroud (40) that encircles the proximal hub (not shown) of cannula (20), a cap plate (42) secured to a proximal end of distal shroud (40), and a latch ring (44) rotatably disposed therebetween and having a radially outwardly projecting tab (46). Latch ring (44) is selectively rotatable via tab (46) about the central axis (A) of trocar (10) between a locked position and an unlocked position. In the locked position, latch ring (44) locks proximal housing portion (32) to distal housing portion (34). In the unlocked position, latch ring (44) permits separation of proximal housing portion (32) from distal housing portion (34), for example to directly access a distal seal structure (not shown) housed within distal housing portion (34). In some versions, distal shroud (40) may be formed integrally with the proximal end of cannula tube (22) such that distal shroud (40) is a component of cannula (20).

Though not shown, proximal housing portion (32) houses a proximal (or "outer") seal structure, and distal housing portion (34) houses a distal (or "inner") seal structure, both arranged along the central axis (A) of trocar (10). The proximal and distal seal structures cooperate to define a seal assembly that maintains insufflation of the patient's abdominal cavity during a surgical procedure while permitting passage of surgical instruments and tissue fragments along working channel (14). For instance, the proximal seal structure may include an annular seal member configured to sealingly engage the shaft of a laparoscopic surgical instrument directed through working channel (14). The distal seal structure may include a duckbill seal member configured to maintain working channel (14) in a sealed stated in the absence of a surgical instrument shaft.

Cannula assembly (12) further includes an insufflation port (50) operatively coupled with the proximal end of cannula (20) and having an adjustable valve in the form of a stopcock (52). Insufflation port (50) is configured to direct insufflation fluid, such as carbon dioxide, from a fluid source (not shown) distally through working channel (14) and into the patient's abdominal cavity to thereby expand (or "insufflate") the cavity with the fluid. This expansion of the abdominal cavity creates additional space for performing a laparoscopic surgical procedure with improved ease.

As shown in FIGS. 1 and 2, obturator (16) of trocar (10) includes a proximal head (60), an elongate cylindrical shaft (62) extending distally from head (60), and a tapered distal tip (64). Obturator shaft (62) is configured to be received within working channel (14) of cannula assembly (12) such that obturator tip (64) extends through and distally of cannula tip (24). Obturator head (60) includes a domed upper body (66), a base plate (68), and an actuatable latch member (70), which includes a pair of latch arms (72) and a corresponding pair of latch buttons (74). Latch arms (72) are configured to be captured within respective slots (not shown) formed in a top surface of seal housing head (36) to couple obturator (16) with cannula assembly (12). Latch buttons (74) are actuatable to release latch arms (72) from the slots and thereby permit separation of obturator (16) from cannula assembly (12). Obturator (16) further includes a central passage (76) that extends longitudinally through obturator head (60) and obturator shaft (62), and is configured to receive an endoscope (not shown) therein to provide visualization during insertion of trocar (10) through the abdominal wall of a patient. A clamp lever (78) of obturator head (60) is pivotable to selectively fix the endoscope within central passage (76). Central passage (76) and clamp lever (78) are merely optional features and may be omitted from obturator (16) in other versions.

Cannula assembly (12) and obturator (16) may be constructed to be disposed of after a single use with a patient. In other versions, one or more components of trocar (10) may be suitably constructed to withstand sterilization and multiple reuses, for example as described in greater detail below in connection with trocar (110) of FIGS. 4-5.

B. Exemplary Deployment of Trocar Into Patient Abdominal Cavity

FIGS. 3A-3D illustrate an exemplary method of accessing an abdominal cavity (1) of a patient through the patient's abdominal wall (2) with trocar (10) described above. It will be appreciated that abdominal wall (2) includes outward superficial layers and inward deep layers. Superficial layers generally include an outer layer of skin (3) and an inner layer of fat (4); whereas the deeper layers include alternating layers of muscle (5) and fascia (6), which are fibrous and flexible with relatively higher tensile strength than the superficial layers.

Figure 3A:
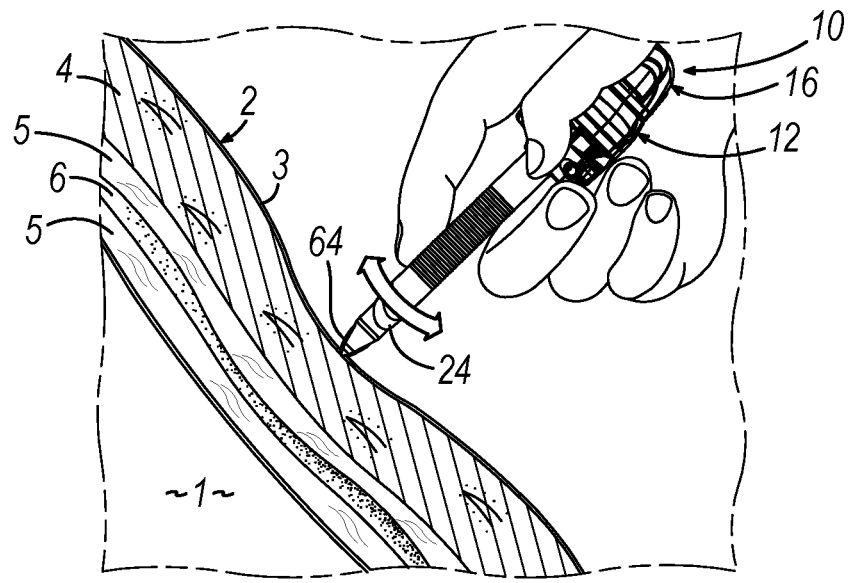
FIG. 3A depicts a side sectional view of the trocar of FIG. 1 being manipulated by a clinician through tissue layers of an abdominal wall.
Figure 3B:
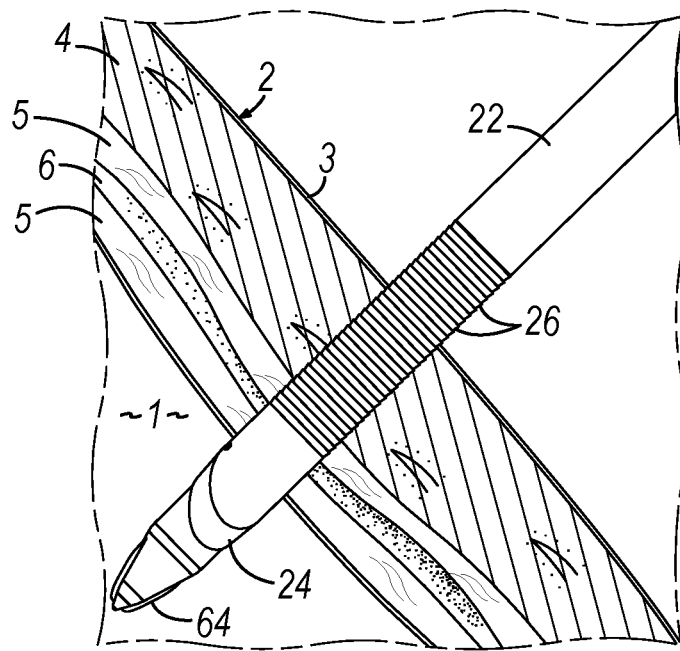
FIG. 3B depicts an enlarged side sectional view of the trocar of FIG. 1, showing a distal end of the trocar received within the abdominal cavity of FIG. 3A.
Figure 3C:
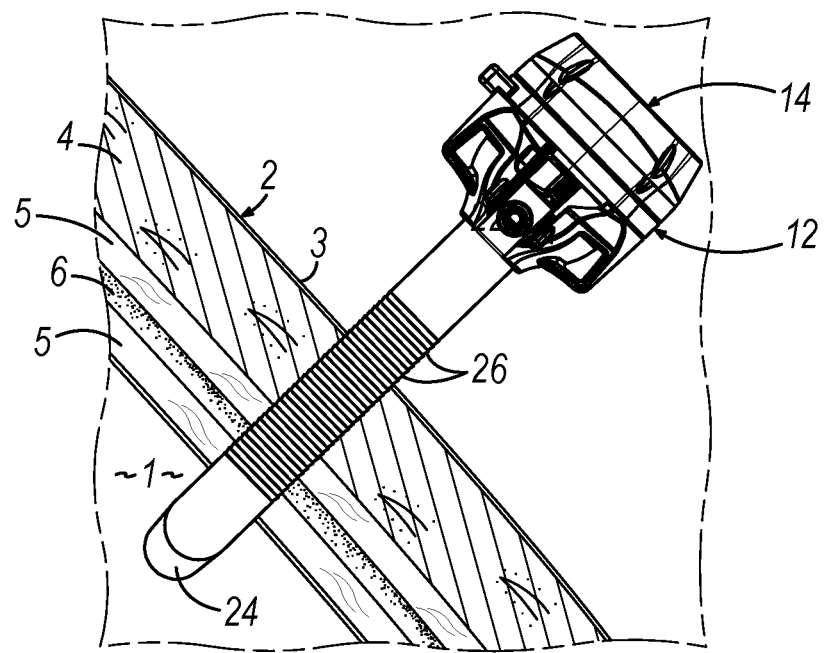
FIG. 3C depicts a side sectional view of the cannula assembly of FIG. 1, showing the cannula assembly remaining positioned within the abdominal wall of FIG. 3A following detachment and removal of the obturator.
Figure 3D:
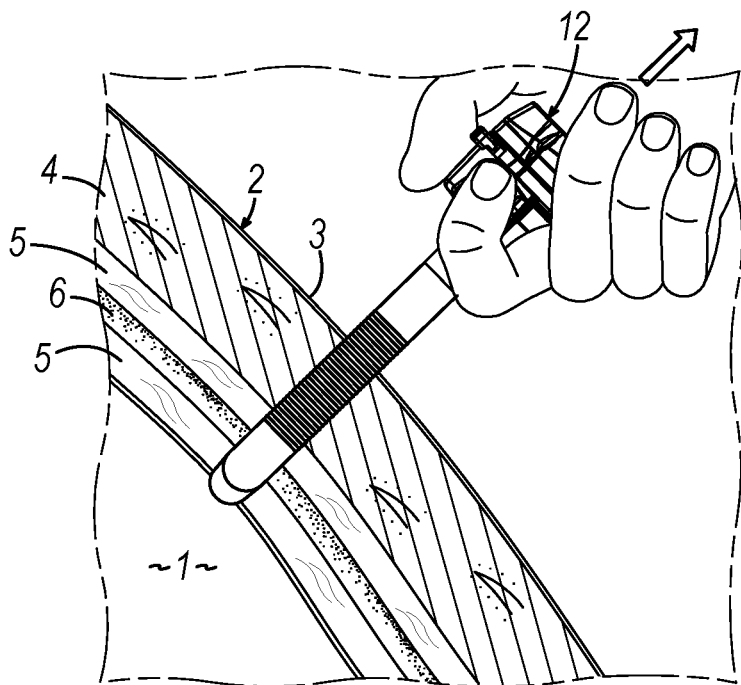
FIG. 3D depicts a side sectional view of the cannula assembly of FIG. 1 being withdrawn proximally from the abdominal wall of FIG. 3A.

As shown in FIG. 3A, with obturator (16) received within cannula assembly (12) and connected to seal housing (30), a clinician manipulates trocar (10) via obturator head (60) and seal housing (30) to urge obturator tip (64) against skin (3) and inward toward abdominal cavity (1) while rotating trocar (10) back and forth. Continued inward urging of trocar (10) further directs obturator tip (64) and cannula tip (24) distally through the layers of fat (4) and fascia (5) and into cavity (1), as shown in FIG. 3B. As discussed above, this step may be facilitated with visualization provided by an endoscope (not shown) mounted within obturator (16). Once cannula (20) has reached a desired depth of insertion into cavity (1), the clinician releases obturator head (60) from seal housing (30) via depression of latch buttons (74), and then withdraws obturator (16) from proximally from cannula assembly (12), as shown in FIG. 3C. This renders working channel (14) of cannula assembly (12) free to receive surgical instruments distally therethrough for performing the laparoscopic surgical procedure. As described above, tissue engagement ribs (26) provided on cannula tube (22) grip the layers of tissue (3, 4, 5) of abdominal wall (2), thus providing cannula assembly (12) with at least a minimum degree of stability relative to abdominal wall (2). Upon completion of the laparoscopic surgical procedure, the clinician grasps seal housing (30) and withdraws cannula assembly (12) proximally from abdominal wall (2), as shown in FIG. 3D.

C. Exemplary Reusable Trocar Having Disposable Seal Assembly

Figure 4:
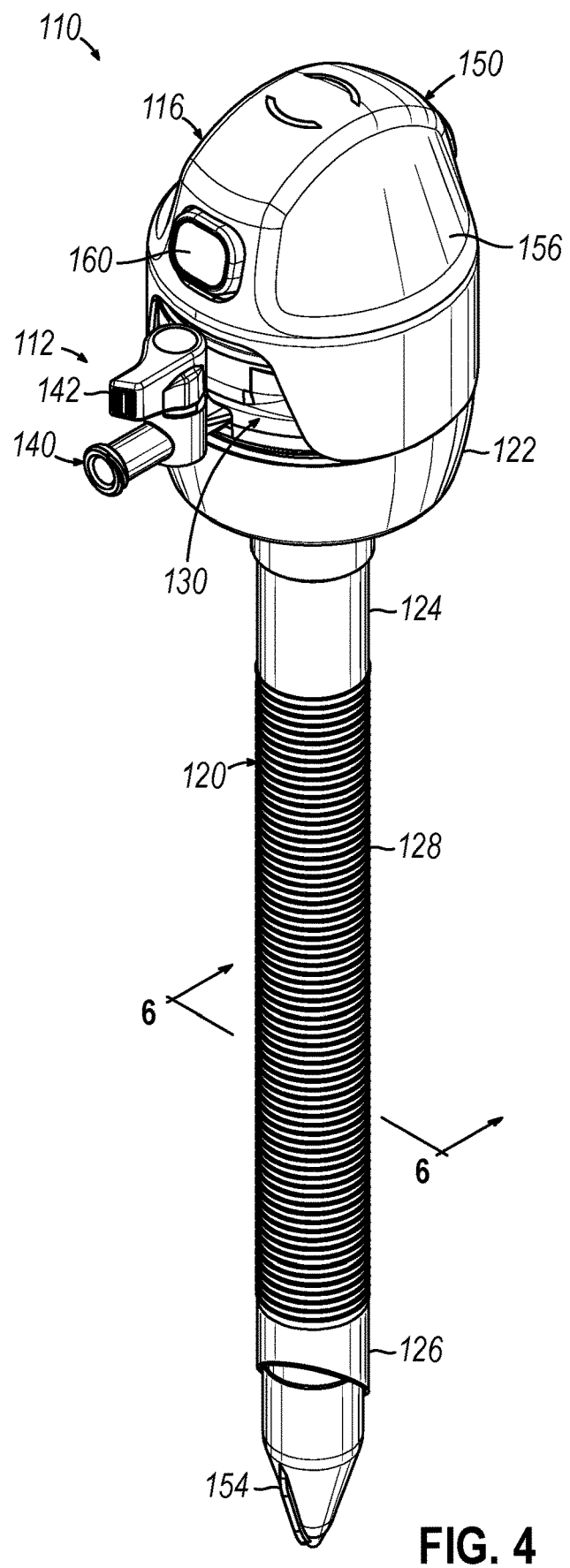
FIG. 4 depicts a perspective view of another exemplary trocar having a cannula assembly and an obturator shown in an assembled state.
Figure 5:
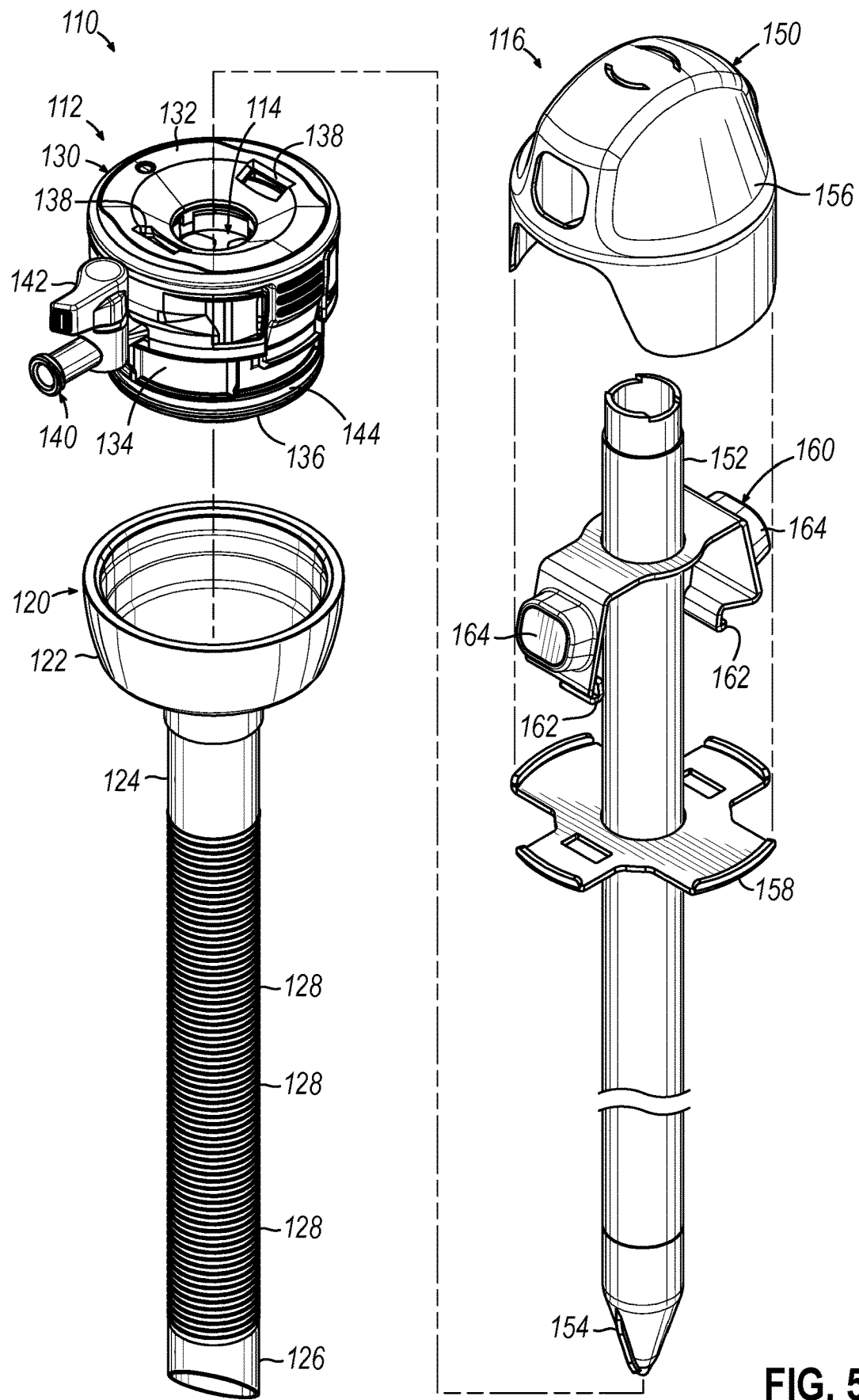
FIG. 5 depicts a perspective view of the cannula assembly and the obturator of FIG. 4 in a disassembled state, showing a reusable cannula and a disposable seal assembly of the cannula assembly separated from one another, and showing the obturator in an exploded state.

In some instances, it may be desirable to configure a trocar such that one or more components thereof may be sterilized and reused for multiple surgical procedures, while one or more other components may be easily and economically disposed of and replaced after each procedure. FIGS. 4-5 show another exemplary trocar (110) that is configured in such a manner, and which is similar in structure and function to trocar (10) described above except as otherwise described below.

Similar to trocar (10), trocar (110) includes a cannula assembly (112) having a working channel (114) and an obturator (116) configured to be inserted into cannula assembly (112) coaxially along working channel (114). Cannula assembly (112) includes a cannula (120) having a bell-shaped hub (122) at a proximal end thereof, and an elongate cylindrical tube (124) extending distally from hub (122) and terminating at an angled cannula tip (126). An outer surface of cannula tube (124) includes a plurality of tissue gripping features in the form of annular ribs (128) arranged axially along a medial portion of cannula tube (124) and which are similar to ribs (26) described above.

Cannula assembly (112) further includes a seal assembly (130). Unlike the seal assembly defined by seal housing (30) of trocar (10), seal assembly (130) is constructed as a modular, replaceable unit configured to releasably mate with proximal hub (122) of cannula (120). As shown best in FIG. 5, seal assembly (130) of the present example generally includes an upper frame member (132), a middle frame member (134), and a lower frame member (136) secured relative to one another in a coaxial arrangement. Though not shown, a proximal (or "outer") seal structure is supported within upper frame member (132), and a distal (or "inner") seal structure is supported within lower frame member (136). Such seal structures may be similar in structure and function to the proximal and distal seal structures of trocar (10) described above. Seal assembly (130) further includes an insufflation port (140) having an adjustable valve in the form of a stopcock (142).

A lower portion of seal assembly (130) distal to insufflation port (140) is configured to seat within proximal hub (122) of cannula (120) such than an annular seal member (144) disposed circumferentially about the lower portion sealingly engages an inner surface of cannula hub (122). In this manner, an interior of seal assembly (130) fluidly communicates with a lumen of cannula (120) to define a working channel (114) of cannula assembly (112) through which insufflation fluid, surgical instruments, and tissue fragments may be directed in the manners generally described above in connection with trocar (10). Seal assembly (130) may be further configured in accordance with one or more teachings of U.S. Pat. Pub. No. 2019/0090905, entitled "Trocar Seal Assemblies," published Mar. 28, 2019, issued as U.S. Pat. No. 10,792,069 on Oct. 6, 2020, the disclosure of which is incorporated by reference herein; and/or U.S. Pat. Pub. No. 2019/0380742, entitled "Asymmetric Shaft Seal," published Dec. 19, 2019, issued as U.S. Pat. No. 10,820,924 on Nov. 3, 2020, the disclosure of which is incorporated by reference herein.

As shown best in FIG. 5, obturator (116) of trocar (110) includes a proximal head (150), an elongate cylindrical shaft (152) extending distally from head (150), and a tapered tip (154) at a distal end of shaft (152). Obturator head (150) includes a domed upper body (156), a base plate (158), and an actuatable latch member (160), which includes a pair of downwardly extending latch arms (162) and a corresponding pair of latch buttons (164). Latch arms (162) are configured to be captured within respective slots (138) formed in a top surface of upper frame member (132) of seal assembly (130) to couple obturator (116) with cannula assembly (112). Latch buttons (164) are actuatable to release latch arms (162) from slots (138) and thereby permit separation of obturator (116) from cannula assembly (112).

Cannula (120) and obturator (116) of the present example are suitably constructed of a robust material, such as surgical steel, such that they may be sterilized and reused for multiple surgical procedures. In contrast, as described above, seal assembly (130) is constructed as a disposable unit, intended to be separated from cannula (120) and replaced after each procedure. For instance, seal assembly (130) may be constructed of various polymeric materials, including plastics and rubbers, such that seal assembly (130) may be easily manufactured and sold at a price point that renders seal assembly (130) suitable for disposal after a single use, similar to trocar (10) described above.

II. Exemplary Balancing Feature for Reusable Trocar

Figure 6:
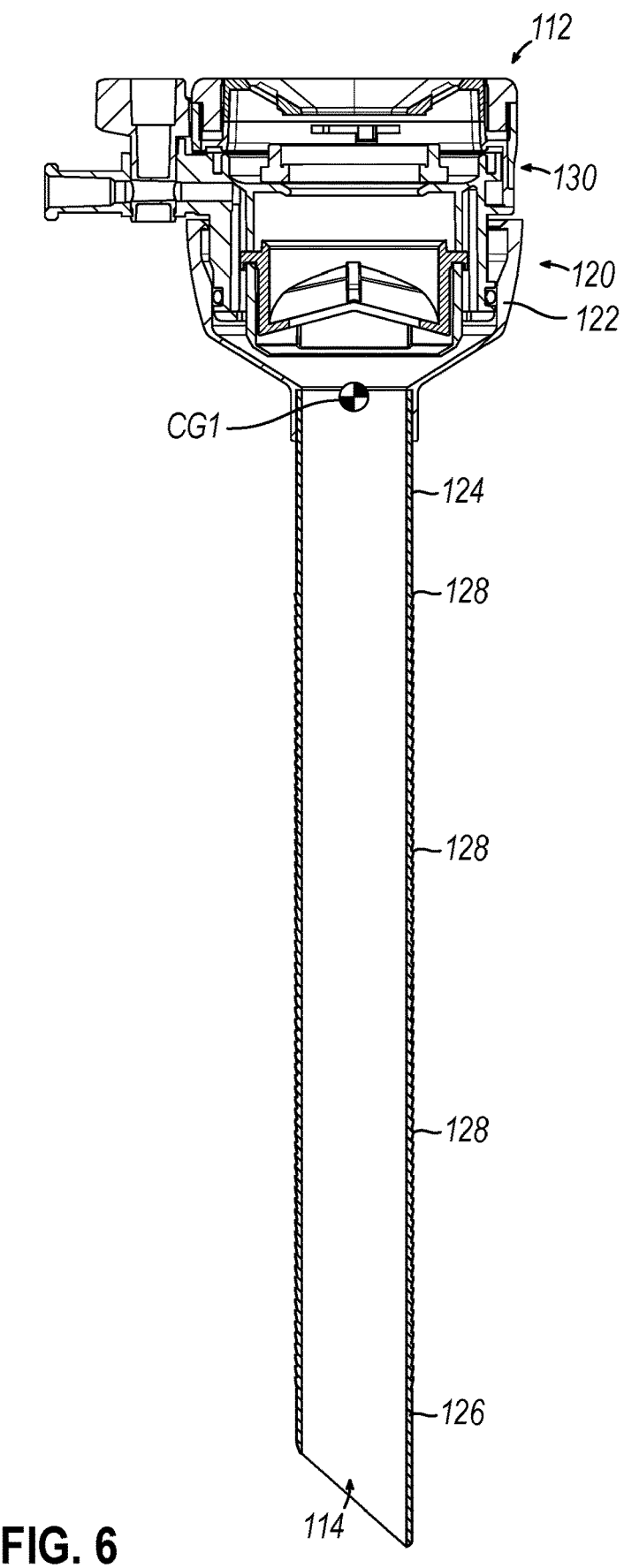
FIG. 6 depicts a cross-sectional view of the cannula assembly of FIG. 4, taken along line 6-6 of FIG. 4.

As best shown in FIG. 6, the center of gravity (CG1) of cannula assembly (112) is located near the proximal end of elongate cylindrical tube (124) and a bell-shaped hub (122). Additionally, the cross-sectional thickness of elongate cylindrical tube (124) may be substantially uniform at the proximal end and the distal end of elongate cylindrical tube (124), with slight deviations in cross-sectional thickness to accommodate for annular ribs (128). In other words, the inner dimeters and the outer diameters of the proximal portion and the distal portion of cylindrical tube (124) may be substantially the same.

Since cannula (120) and obturator (116) are constructed from a robust material, cannula (120) and obturator (116) may have a greater mass and resulting weight compared to cannula (12) and obturator (16) of single use trocar (10) described above. As will be described in greater detail below, the greater mass and weight of cannula (120) may cause instability and/or lack of balance of cannula (120) relative to abdominal wall (2) in transverse (i.e., radial, or lateral) directions such that cannula (120) may tip or tilt to a side and thus cause working channel (114) to become misaligned with a targeted operating area (T) during exemplary use in accordance with the description herein.

Figure 7A:
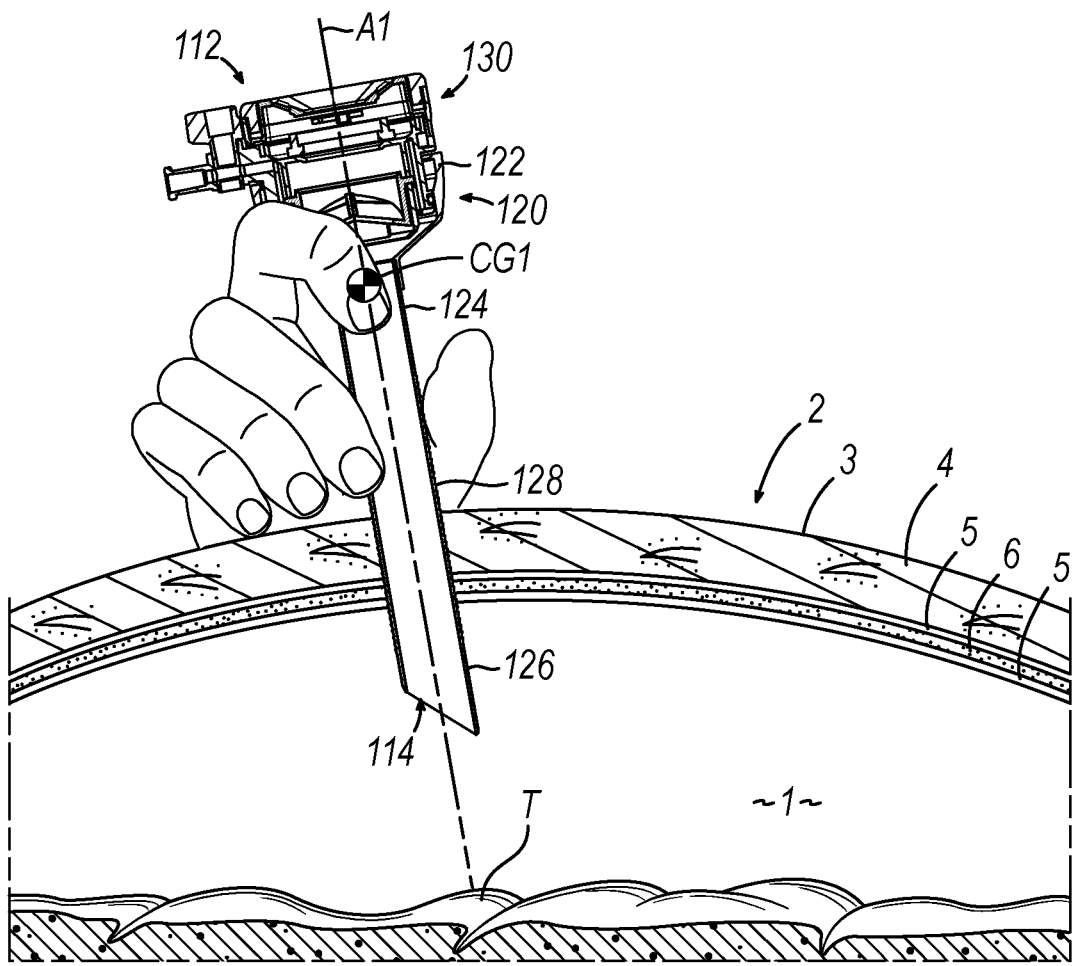
FIG. 7A depicts a sectional view of the cannula assembly of FIG. 4 positioned within the abdominal wall of a patient, with the clinician holding the cannula assembly, where the cannula assembly is suitably aligned with a target area.

FIG. 7A shows cannula assembly (112) providing suitable access into cavity (1) of the patient via working channel (114) in accordance with the teachings herein. Therefore, prior to accessing the position shown in FIG. 7A, obturator (116) and cannula assembly (112) may have been used in conjunction with each other such that obturator tip (154) and cannula tip (126) are urged distally through skin (3), the layers of fat (4) and fascia (5) in order to access cavity (1). Once access is provided, the clinician may remove obturator (116) in accordance with the description herein. Next, as shown in FIG. 7A, the clinician may place cannula assembly (112) in the desired location relative to patient such that central axis (A1) is aligned with the targeted operating area (T). Similar to tissue engagement ribs (26) described above, tissue engagement ribs (128) provided on cannula tube (124) grip the layers of tissue (3, 4, 5) of abdominal wall (2), thus providing cannula assembly (112) with at least a minimum degree of stability in axial and transverse directions relative to abdominal wall (2).

Figure 7B:
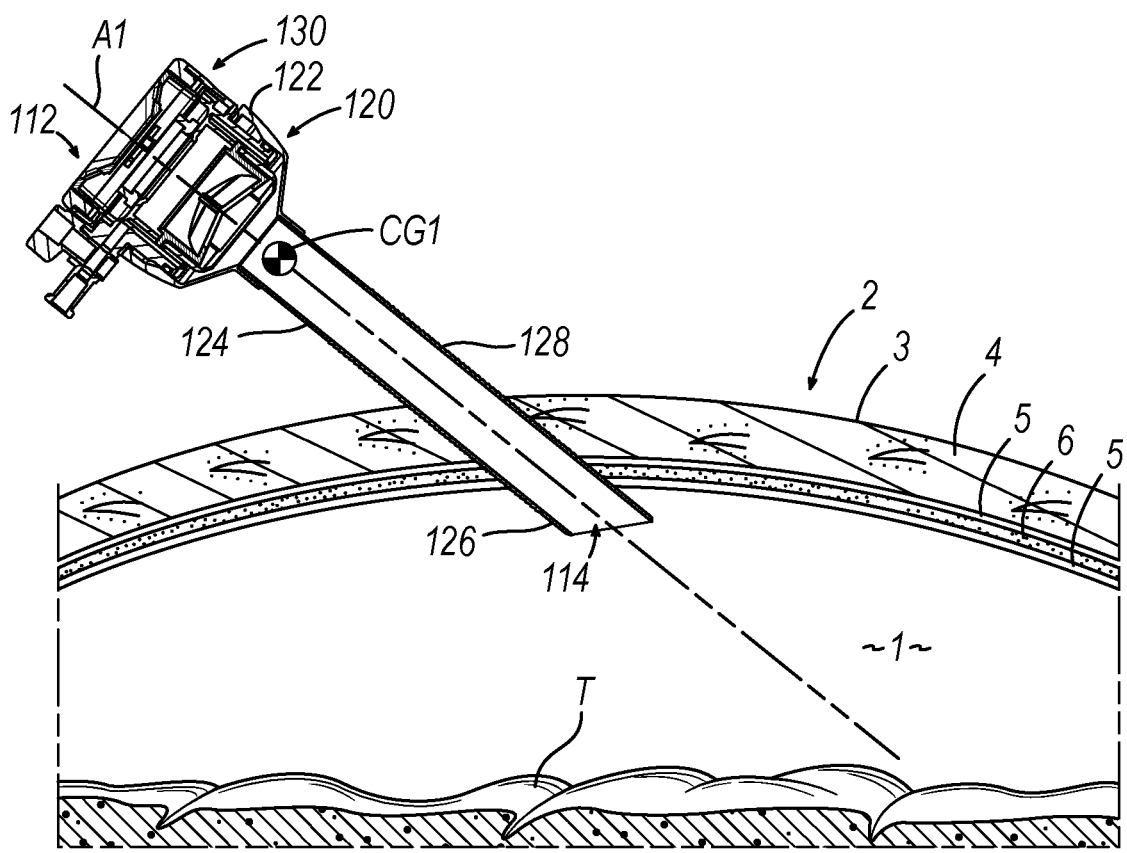
FIG. 7B depicts a sectional view of the cannula assembly of FIG. 4 positioned within the abdominal wall of the patient, where the clinician has released the cannula assembly such that the cannula assembly has tipped over and is no longer suitably aligned with the target area of FIG. 7A.
Figure 8:
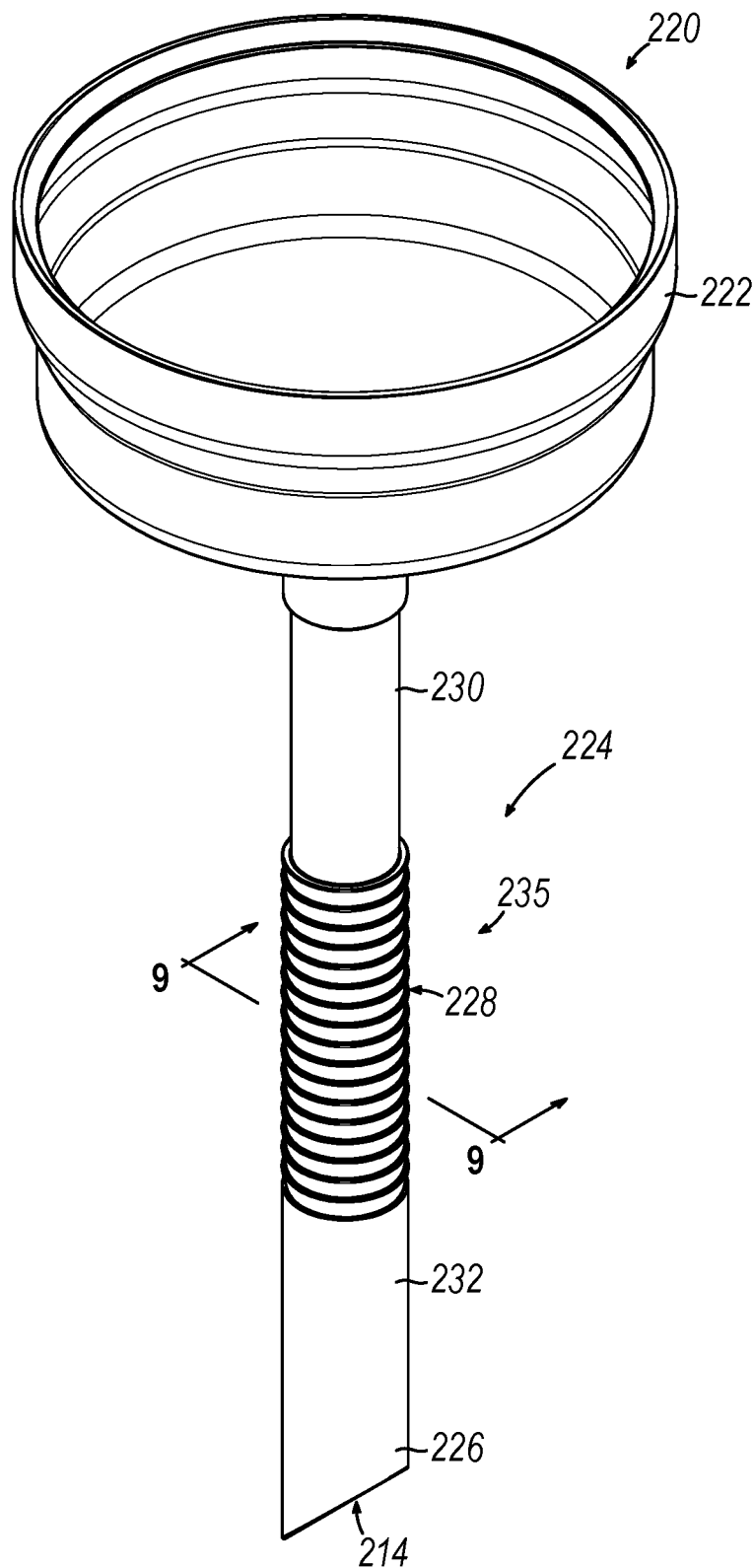
FIG. 8 depicts a perspective view of an exemplary cannula.

During exemplary use, it may be desirable for central axis (A1) to maintain proper alignment with targeted operating area (T) after the clinician releases cannula assembly (112) in order to access cavity (1) via working channel (114) in accordance with the description herein. However, in some instances, as shown between FIGS. 7A-7B, when the clinician releases cannula assembly (112), cannula assembly (112) may become unbalanced and "tip over" such that working channel (114) becomes misaligned with a targeted operating area (T).

In instances where the center of gravity (CG1) is laterally spaced away from the portion of tissue engagement ribs (128) that engage abdominal wall (2), a fulcrum force and a resulting torque may be created. The fulcrum force, as created by the weight of cannula assembly (112) and acting at the center of gravity (CG1), is imparted as a torque on the portion of ribs (128) that engage abdominal wall (2) and may become too great such that cannula assembly (112) tips over, thereby misaligning working channel (114) with targeted operating area (T). Cannula assembly (112) may be more prone to tipping over compared to cannula assembly (12) described above partially due to the increased weight of cannula assembly (112), which in turn creates a greater fulcrum force acting at the center of gravity, and thus a greater tipping torque about the portion of cannula assembly (112) positioned within the abdominal wall (2). Therefore, the location of center of gravity that was acceptable for a light weight, single-use cannula (20) may not be acceptable for heavier cannula (120) formed from robust material to promote sterilization and reuse for multiple surgical procedures.

As mentioned above, cannula assembly (112) may become unbalanced and "tip over" such that working channel (114) becomes undesirably misaligned with a targeted operating area (T). Therefore, it may be desirable for cannula assembly (112) to have a balancing feature that may help promote desirable placement of cannula assembly (112) relative to abdominal wall (2) such that (A) working channel (114) may remain suitably aligned with the targeted operating area (T) during exemplary use in accordance with the description herein, and (B) cannula (120) may be formed of a robust material for purposes of sterilization and reuse.

FIGS. 8-11 show an exemplary cannula (220) that may be used in replacement of cannula (120) described above; while FIGS. 12A-12B show an exemplary use of a cannula assembly (212) formed from cannula (220) and seal housing (130). Cannula (220) includes a bell-shaped hub (222) at a proximal end thereof, and an elongate cylindrical tube (224)

extending distally from hub (222) and terminating at an angled cannula tip (226); all of which define working channel (214). An outer surface of cannula tube (224) includes a plurality of tissue gripping features in the form of annular ribs (228) arranged axially along a medial portion of cannula tube (224). Bell-shaped hub (222), elongated cylindrical tube (224), angled cannula tip (226), working channel (214), and annular ribs (228) may be substantially similar to bell-shaped hub (122), elongated cylindrical tube (124), angled cannula tip (126), working channel (114) and annular ribs (128) described above, with differences elaborated below.

Cannula (220) also includes a balancing feature (235) that is integrated into cannula tube (224). As will be described in greater detail below, balancing feature (235) is configured to inhibit cannula assembly (212) from tipping over when a clinician releases cannula assembly (212), such that working channel (214) may remain aligned with a targeted operating area (T).

Balancing feature (235) includes a proximal thinner section (230) having a relatively thinner wall thickness, a distal thicker section (232) having a relatively thicker wall thickness, and a transition section (234) between the proximal and distal sections (230, 232). Proximal thinner section (230) may extend from bell-shaped hub (222) to a proximal portion of elongate cylindrical tube (224), while distal thicker section (232) may extend along a distal portion of elongate cylindrical tube (224).

Bell-shaped hub (222) includes a distally presented stem (225) dimensioned to receive a proximal end of elongate cylindrical tube (224). Bell-shaped hub (222) is fixed to cylindrical tube (224) via distally presented stem (225) via coupling (236). Any suitable coupling (236) may be used as would be apparent to one skilled in the art in view of the teachings herein. For example, coupling (236) may include a weld, an adhesive, and interference fit, etc.

Figure 9:
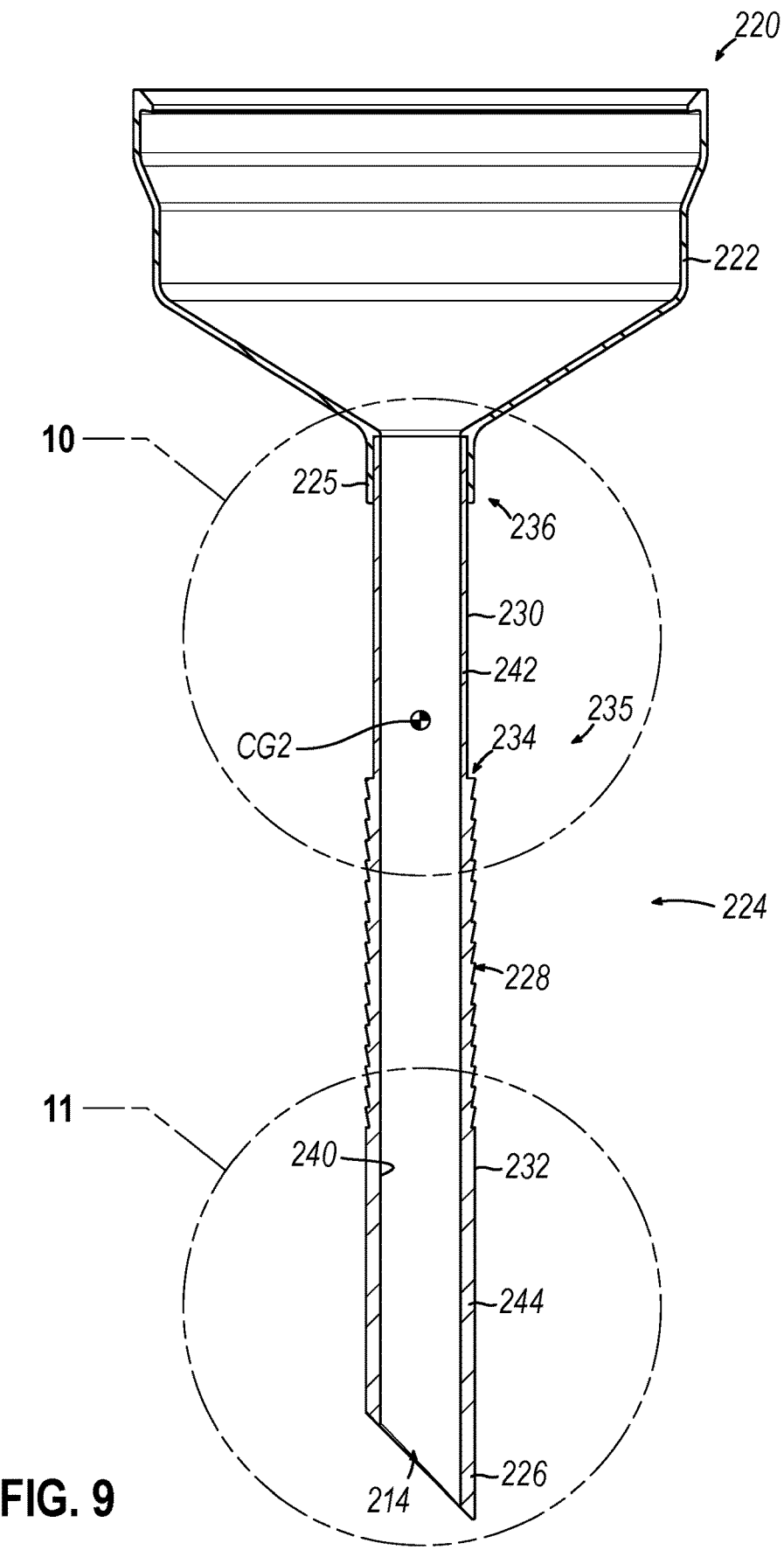
FIG. 9 depicts a cross-sectional view of the cannula of FIG. 8, taken along line 9-9 of FIG. 8.

As best shown in FIG. 9, proximal thinner section (230) may be dimensioned to have a smaller wall thickness as compared to distal thicker section (232). The reduced wall thickness of proximal thinner section (230) may allow for the proximal portion of cannula (220) to be formed with less material as compared to corresponding portions of cannula (120) described above. Therefore, the weight of proximal thinner section (230) may be smaller compared to corresponding portions of cannula (120) described above.

In the current example, bell-shaped hub (222) and the portion of cylindrical tube (224) defining proximal thinner section (230) have a similar wall thickness. However, this is merely optional. In some instances, bell-shaped hub (222) may have a different wall thickness compared to the portion of cylindrical tube (224) defining proximal thinner section (230). In some instances, bell-shaped hub (222) may be truncated to be formed from less material. In some instances, bell-shaped hub (222) may be entirely optional such that seal housing (130) is configured to operatively couple with the proximal end of elongate tube (224) without the need of a complete bell-shaped hub (222).

Distal thicker section (232) may be formed to have a greater wall thickness compared to proximal thinner section (230). The increased wall thickness of distal thicker section (232) may allow for the distal portion of cannula (220) to be formed with more material compared to corresponding portions of cannula (120) described above. Therefore, the weight of distal thicker section (232) may be greater compared to corresponding portions of cannula (120) described above.

Figure 10:
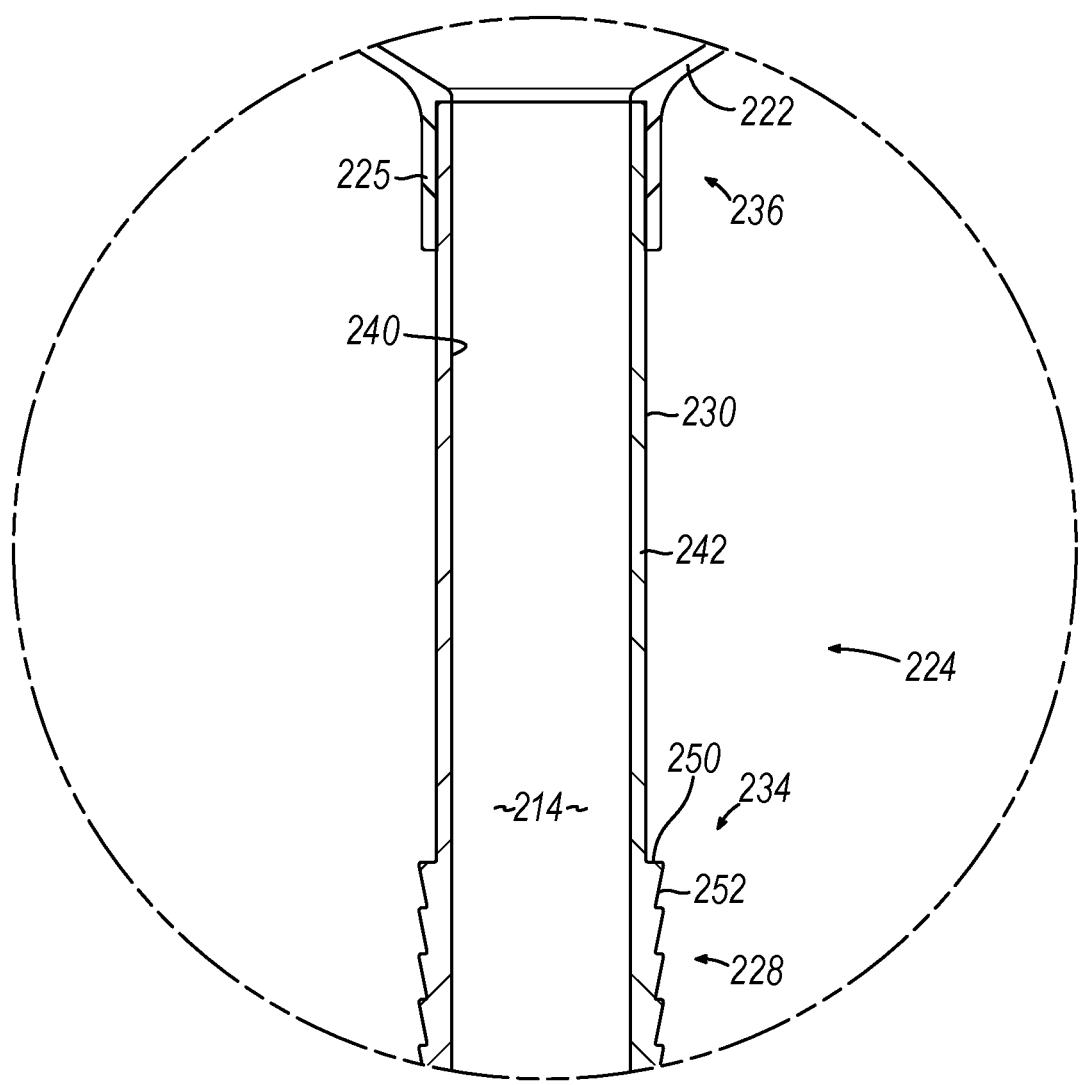
FIG. 10 depicts an enlarged cross-sectional view of a proximal portion of the cannula of FIG. 8.

Transition portion (234) is located between proximal thinner section (230) and distal thicker section (232). In the current example, as shown in FIG. 10, transition portion (234) is located just proximally to the proximal end of annular ribs (228). While in the current example, transition portion (234) is located adjacent to the proximal end of annular ribs (228), transition portion (234) may be placed at any suitable location as would be apparent to one skilled in the art in view of the teachings herein.

As also shown in FIG. 10, the wall thickness of thinner section (230) defined by tube (224) is determined by the distance between inner surface (240) of tube (224) and proximal outer surface (242) of tube (224). In the current example, the distance between surface (240, 242) is substantially uniform along the length of proximal section (230). In other words, the inner diameter defined by inner surface (240) and the outer diameter defined by proximal outer surface (242) are substantially uniform along the length of proximal section (230). However, this is merely optional. In some instances, the distance between surfaces (240, 242) may deviate along the length of proximal section (230).

Figure 11:
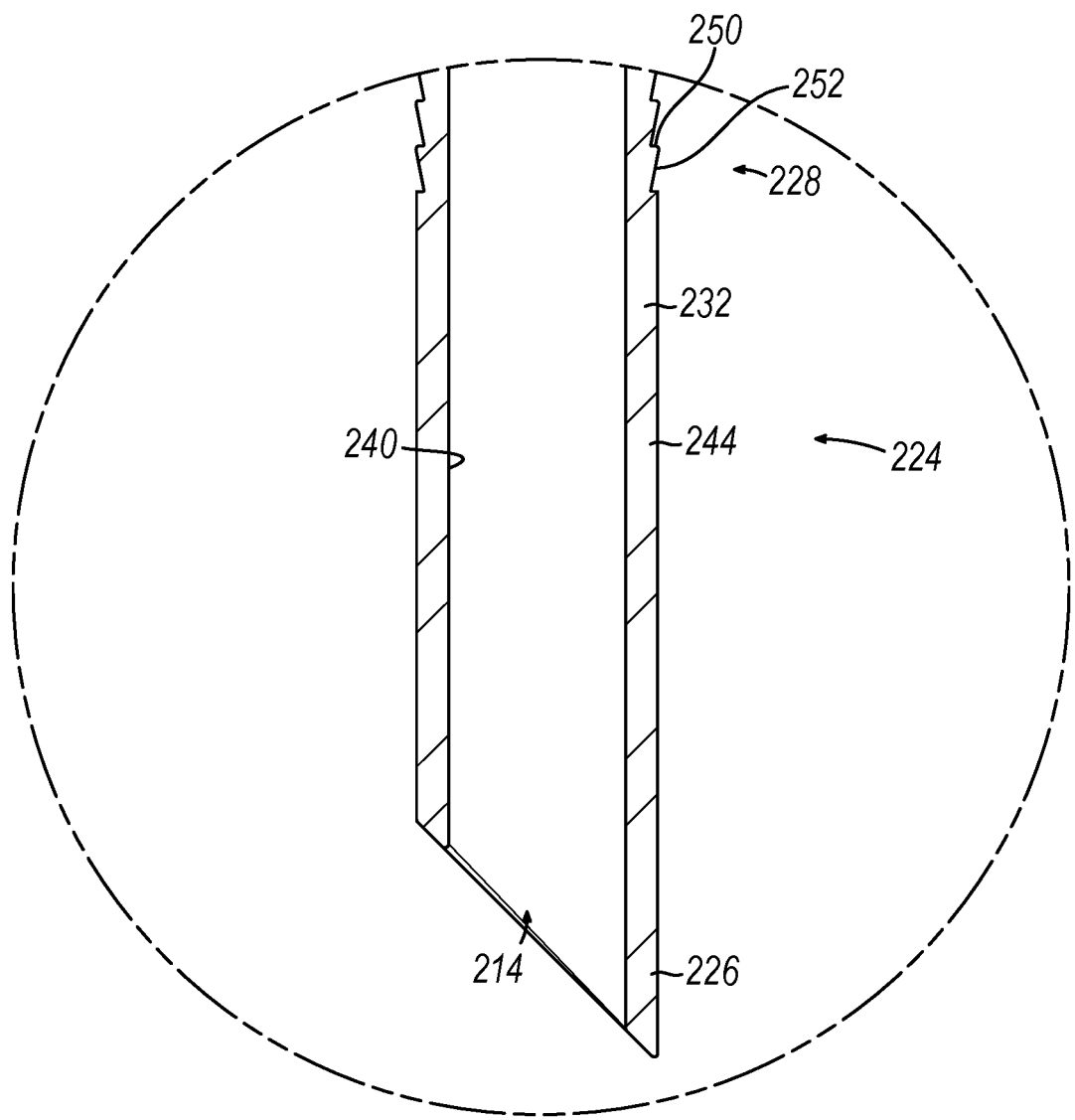
FIG. 11 depicts an enlarged cross-sectional view of a distal portion of the cannula of FIG. 8.

As best shown in FIG. 11, the wall thickness of thicker section (232) is determined by the distance between inner surface (240) of tube (224) and either (A) a distal outer surface (244) of tube (224) or (B) a portion of annular ribs (228). Each annular rib (228) is formed from a shoulder portion (250) and a tapered portion (252), where the shoulder portion (250) and the tapered portion (252) connect at an outer rim. Distal outer surface (244) may not protrude laterally away from working channel (214) further than shoulder portions (250) of annular ribs (228). This may help ensure that annular ribs (228) still grip tissue adequately in order to promote stability of cannula (220) during exemplary use.

In the current example, the distance between surfaces (240, 244) is substantially uniform along the length of tube (224) including distal outer surface (244). In other words, the inner diameter defined by inner surface (240) and the outer diameter defined by distal outer surface (244) are substantially uniform along the length of distal section (232) having distal outer surface (244). However, this is merely optional. In some instances, the distance between surfaces (240, 244) may deviate along the length of distal section (232).

Additionally, in the current example, the dimension of inner surface (240) is substantially uniform along the length of tube (224). In other words, the inner diameter defined by inner surface (240) is substantially uniform along the length of tube (224). However, this is merely optional, as the dimensions of working channel (214) defined by inner surface (240) may have any suitable geometry as would be apparent to one skilled in the art in view of the teachings herein. For instance, inner surface (240) may have a tapered geometry, an undulating geometry, etc.

The shift in weight distribution caused by the change in dimensions of proximal thinner section (230) and distal thicker section (232) may shift the center of gravity (CG2) of cannula (220) distally compared to center of gravity (CG1) of cannula (120) described above. As will be described in greater detail below, this may allow balancing feature (235) to prevent accidental tipping over of cannula assembly (220) during exemplary use.

Figure 12A:
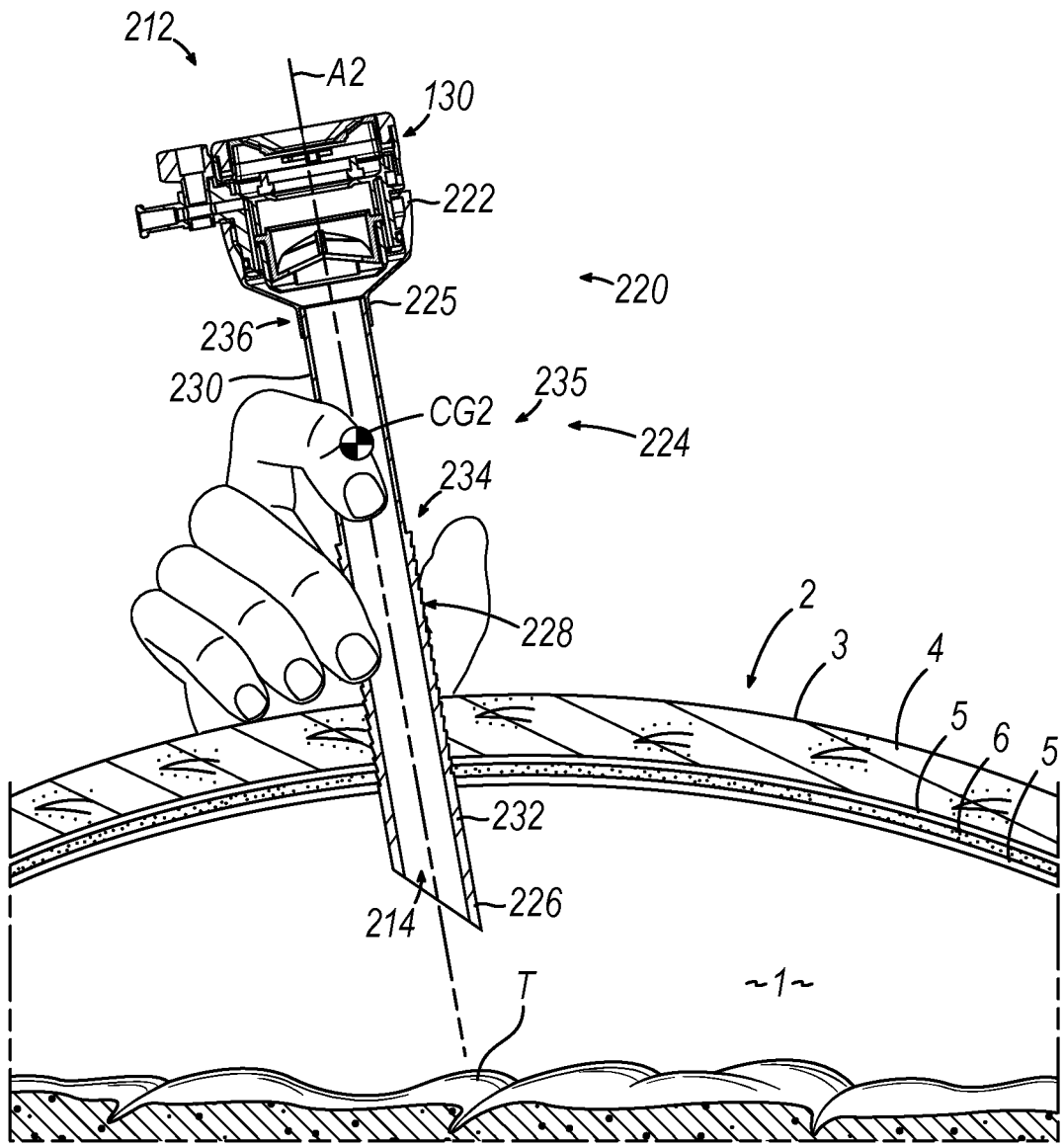
FIG. 12A depicts a sectional view of a cannula assembly formed from the cannula of FIG. 8 and the disposable seal assembly of FIG. 5, where the cannula assembly is positioned within an abdominal wall of a patient, with the clinician holding the cannula assembly, where the cannula assembly is suitably aligned with a target area.
Figure 12B:
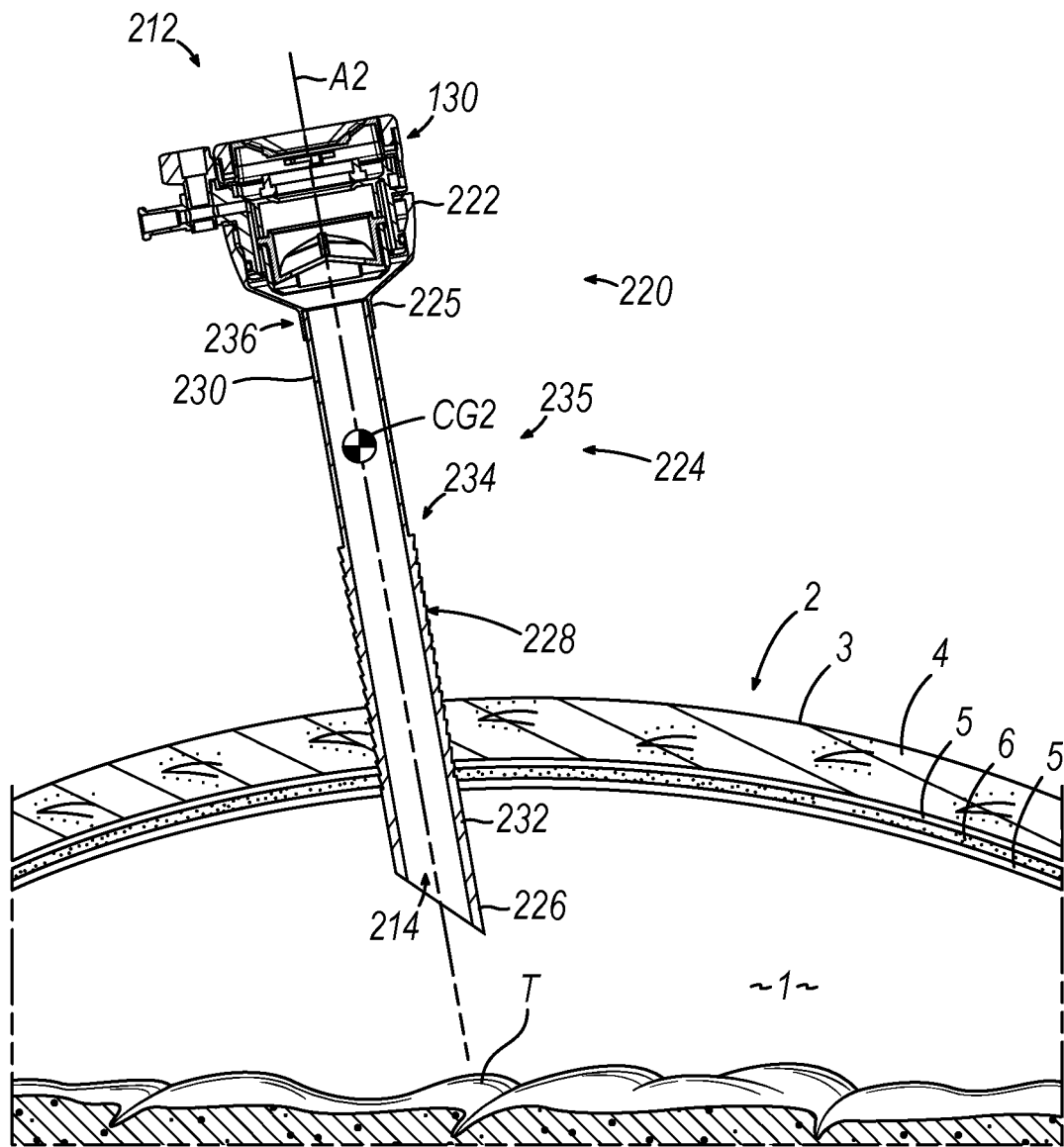
FIG. 12B depicts a sectional view of the cannula assembly of FIG. 12A positioned within the abdominal wall of FIG. 12A, where the cannula assembly has been released by the clinician and remains suitably aligned with the target area.

FIG. 12A shows cannula assembly (212) providing suitable access into cavity (1) of the patient via working channel (214) in accordance with the teachings herein. Therefore, prior to accessing the position shown in FIG. 12A, obturator (116) and cannula assembly (212) may have been used in conjunction with each other such that obturator tip (154) and cannula tip (226) are urged distally through skin (3), the layers of fat (4) and fascia (5) in order to access cavity (1). Once access is provided, the clinician may remove obturator (116) in accordance with the description herein. Next, as shown in FIG. 12A, the clinician may place cannula assembly (212) in the desired location relative to patient such that central axis (A2) is aligned with the targeted operating area (T). Similar to tissue engagement ribs (26) described above, tissue engagement ribs (228) provided on cannula tube (224) grip the layers of tissue (3, 4, 5) of abdominal wall (2), thus providing cannula assembly (212) with at least a minimum degree of stability in axial and transverse directions relative to abdominal wall (2).

During exemplary use, it may be desirable for central axis (A2) to maintain proper alignment with targeted operating area (T) after the clinician releases cannula assembly (212) in order to access cavity (1) via working channel (214) in accordance with the description herein. As shown between FIGS. 12A-12B, when the clinician releases cannula assembly (212), balancing feature (235) of cannula (220) may prevent cannula assembly (212) from tipping over, thereby keeping working channel (214) aligned with a targeted operating area (T).

Placing of the center of gravity (CG2) closer toward the portion of elongate cylindrical tube (224) designed to engage abdominal wall (2) may reduce the fulcrum force and resulting torque imparted on the portion of tissue engagement ribs (228) that engage abdominal wall (2) due to the weight of cannula (220), as compared to the fulcrum force and torque imparted by center of gravity (CG1) of cannula (120) described above. This reduction in fulcrum force may be due, at least in in part, to a reduction in lateral distance between center of gravity (CG2) and the portion of tissue engagement ribs (228) that engage abdominal wall (2). Therefore, shifting the center of gravity (CG2) closer toward the portion of tube (224) that engages abdominal wall (2) may allow the clinician to more easily balance cannula (220) relative to the abdominal wall (2) of a patient to keep working channel (214) in alignment with the targeted operating area (T).

In other words, while the total weight of a cannula (220) formed from a robust, sterilizable, and reusable material may not be able to significantly decrease, the geometry of cannula (220) may be modified to effectively shift the center of gravity (CG2) closer to the portion of tube (224) configured to engage the abdominal wall (2) (i.e., distally), which in turn reduces the fulcrum force and resulting torque imparted on the engagement between tube (224) of cannula (220) and abdominal wall (2) of the patient. Therefore, the modified center of gravity (CG2) may help reduce the chance of cannula assembly (212) tipping over during use.

Figure 13:
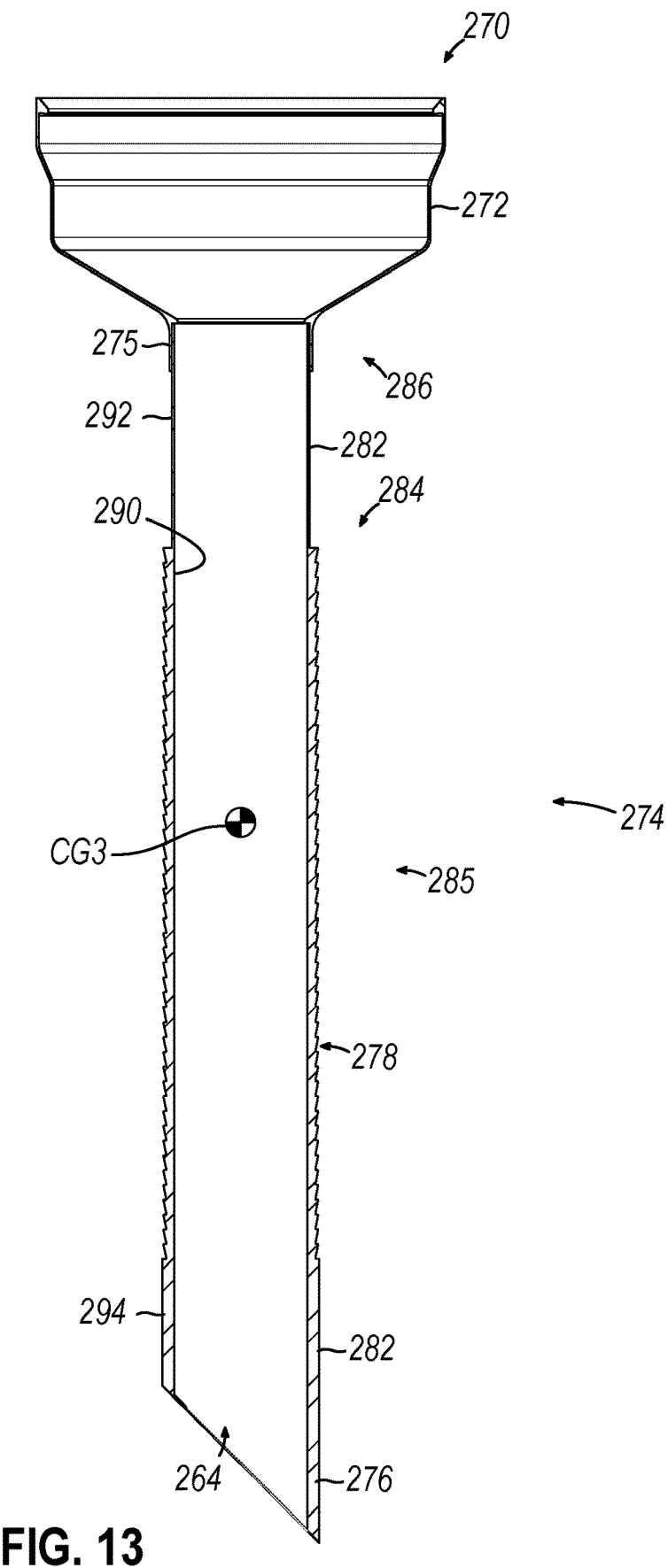
FIG. 13 depicts a cross-sectional view of an exemplary cannula.

FIG. 13 shows another exemplary cannula (270) that may be used in replacement of cannulas (120, 220) described above. Cannula (270) is substantially similar to cannula (220) described above, except balancing feature (285) includes a greater difference in mass and resulting weight between a proximal thinner section (280) and a distal thicker section (282), such that the center of gravity (CG3) is distally shifted further.

Cannula (270) includes a bell-shaped hub (272) at a proximal end thereof, and an elongate cylindrical tube (274) extending distally from hub (272) and terminating at an angled cannula tip (276); all of which define working channel (264). An outer surface of cannula tube (274) includes a plurality of tissue gripping features in the form of annular ribs (278) arranged axially along a medial portion of cannula tube (274). Bell-shaped hub (272), elongated cylindrical tube (274), angled cannula tip (276), working channel (264), and annular ribs (278) may be substantially similar to bell-shaped hub (222), elongated cylindrical tube (224), angled cannula tip (226), working channel (214) and annular ribs (228) described above, with differences elaborated below.

Balancing feature (285) includes a proximal thinner section (280), a distal thicker section (282), and a transition section (284); which may be substantially similar to proximal thinner section (230), distal thicker section (232), and transition section (234) described above, with differences elaborated herein. Therefore, bell-shaped hub (272) is coupled to tube (274) via coupling (286), while the thickness of thinner section (280) defined by tube (274) is determined by the distance between inner surface (290) of tube (274) and proximal outer surface (292) of tube (274). Additionally, the wall thickness of thicker section (282) is determined by the distance between inner surface (290) of tube (274) and either (A) a distal outer surface (294) of tube (274) or (B) a portion of annular ribs (278).

As mentioned above, balancing feature (285) include a greater difference in mass and resulting weight between a proximal thinner section (280) and a distal thicker section (282), such that the center of gravity (CG3) is further distally shifted. In the current example, this is accomplished by having a larger distal thicker section (282), both in length and wall thickness, as compared the proximal thinner section (280). Therefore, it should be understood that the geometry of cannula (270) may be modified in order to adjust the center of gravity (CG3) to a desired location along tube (274) to provide for optimal balancing of cannula (270) by minimizing the fulcrum force and resulting torque imparted on the portion of tube (274) that engages abdominal wall (3) due to the weight of cannula (270).

Proximal thinner section (230, 280) and distal thicker section (232, 282) may have any suitable dimensions as would be apparent to one skilled in the art in view of the teachings herein. Additionally, proximal thinner section (230, 280) and distal thicker section (232, 282) may form any suitably wall thickness ratio as would be apparent to one skilled in the art in view of the teachings herein. For example, proximal thinner section (230, 280) may have a wall thickness of 0.020 inches, while distal thicker section (232, 282) may have a wall thickness of 0.042 inches, creating a wall thickness ratio of 0.47619. As another example, proximal thinner section (230, 280) may have a wall thickness of 0.010 inches, while distal thicker section (232, 282) may have a wall thickness of 0.045 inches, creating a wall thickness ratio of 0.2222. Other suitable wall thickness ratios include, but are not limited to, 1:2, 1:4, 1:5, etc.

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

EXAMPLE 1

A surgical access device assembly comprising: (a) a cannula hub; and (b) a cannula tube extending distally from the cannula hub along a longitudinal axis, wherein the cannula tube defines a working channel configured to guide a surgical instrument along the longitudinal axis of the cannula tube, wherein the cannula tube comprises: (i) a tissue engagement feature disposed along an outer surface of the cannula tube, wherein the tissue engagement feature is configured to stabilize the cannula tube and the cannula hub relative to a body cavity wall of a patient when the cannula tube is inserted distally through the body cavity wall, and (ii) a balancing feature configured to promote lateral stability of the cannula tube and the cannula hub relative to the body cavity wall of the patient, wherein the balancing feature comprises: (A) a proximal portion of the cannula tube having a first wall thickness, wherein at least a portion of the proximal portion is disposed proximal to the tissue engagement feature, and (B) a distal portion of the cannula tube having a second wall thickness, wherein the second wall thickness of the distal portion is greater than the first wall thickness of the proximal portion, wherein at least a portion of the distal portion is disposed distal to the tissue engagement feature.

EXAMPLE 2

The surgical access device of Example 1, wherein the cannula tube comprises an inner surface defining the working channel, wherein the inner surface extends from the proximal portion to the distal portion, wherein the inner surface comprises a uniform inner diameter extending between the proximal portion and the distal portion.

EXAMPLE 3

The surgical access device of any one or more of Examples 1 through 2, wherein the balancing feature comprises a transition portion located between the proximal portion and the distal portion, wherein the transition portion coincides with a proximal end of the tissue engagement feature.

EXAMPLE 4

The surgical access device of any one or more of Examples 1 through 3, wherein the tissue engagement feature comprises a tissue engagement rib comprising a shoulder portion and a tapered portion coupled with each other at an outer rim.

EXAMPLE 5

The surgical access device of Example 4, wherein the proximal portion comprises a proximal outer surface, wherein the distal portion comprises a distal outer surface, wherein the proximal outer surface is closer the working channel compared to the distal outer surface.

EXAMPLE 6

The surgical access device of Example 5, wherein the distal outer surface is closer to the working channel than the outer rim of the tissue engagement rib.

EXAMPLE 7

The surgical access device of any one or more of Examples 1 through 6, wherein cannula hub comprises a bell-shaped body dimensioned to receive a disposable seal assembly.

EXAMPLE 8

The surgical access device of Example 7, wherein the cannula hub further comprises a distal stem coupled to the proximal portion of the cannula tube.

EXAMPLE 9

The surgical access device of any one or more of Examples 1 through 8, wherein the surgical access device is formed from surgical steel.

EXAMPLE 10

The surgical access device of any one or more of Examples 1 through 9, wherein the cannula tube terminates into an angled cannula tip.

EXAMPLE 11

The surgical access device of any one or more of Examples 1 through 10, wherein the tissue engagement feature comprises a plurality of tissue engagement ribs extending along a segment of the distal portion.

EXAMPLE 12

The surgical access device of Example 11, wherein the plurality of tissue engagement ribs terminates distally relative to the proximal portion of the cannula tube.

EXAMPLE 13

The surgical access device of any one or more of Examples 1 through 12, further comprising an obturator wherein the obturator is configured to removably couple with the cannula tube along the longitudinal axis to facilitate insertion of the surgical access device through a body wall of the patient.

EXAMPLE 14

The surgical access device of any one or more of Examples 1 through 13, wherein the cannula hub is configured to selectively couple with a seal assembly.

EXAMPLE 15

The surgical access device of any or more of Examples 1 through 14, wherein the proximal portion and the distal portion define a wall thickness ratio of 1:2.

EXAMPLE 16

A surgical access device assembly comprising: (a) a cannula hub; and (b) a cannula tube extending distally from the cannula hub along a longitudinal axis, wherein the cannula tube defines a working channel configured to guide a surgical instrument along the longitudinal axis the cannula tube, wherein the cannula tube comprises: (i) a proximal portion of the cannula tube having a first wall thickness, (ii) a tissue engagement feature disposed along an outer surface of the cannula tube, wherein the tissue engagement feature is configured to stabilize the cannula tube and the cannula hub relative to a body cavity wall of a patient when the cannula tube is inserted distally through the body cavity wall, and (iii) a distal portion of the cannula tube having a second wall thickness, wherein the tissue engagement feature is interposed between the proximal portion and the distal portion, wherein the second wall thickness of the distal portion is greater than the first wall thickness of the proximal portion.

EXAMPLE 17

The surgical access device of Example 16, wherein the tissue engagement feature comprises a plurality of tissue engagement ribs.

EXAMPLE 18

The surgical access device of Example 16, wherein a maximum wall thickness of the tissue engagement ribs is greater than the second wall thickness of the distal portion.

EXAMPLE 19

The surgical access device of any one or more of Examples 16 through 18, wherein the cannula hub comprises a bell-shaped body.

EXAMPLE 20

A surgical access device assembly comprising: (a) a cannula hub; and (b) a cannula tube extending distally from the cannula hub along a longitudinal axis, wherein an inner surface of the cannula tube defines a working channel configured to guide a surgical instrument along the longitudinal axis of the cannula tube, wherein the cannula tube comprises: (i) a proximal portion of the cannula tube comprising a first wall thickness defined by the inner surface and a proximal outer surface, and (ii) a distal portion of the cannula tube comprising a second wall thickness defined by the inner surface and a distal outer surface, wherein the distal portion terminates into an open distal end wherein the second wall thickness of the distal portion is greater than the first wall thickness of the proximal portion.

IV. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Furthermore, any one or more of the teachings herein may be combined with any one or more of the teachings disclosed in U.S. patent application Ser. No. 17/213,302, entitled "Pinch-To-Release Cannula Depth Limiter," filed on Mar. 26, 2021, published as U.S. Pub. No. 2021/0338272 on Nov. 4 2021; U.S. patent application Ser. No. 17/213,304, entitled "Multi-Diameter Cannula Depth Limiter," filed on Mar. 26, 2021, published as U.S. Pub. No. 2021/0338281 on Nov. 4, 2021; U.S. patent application Ser. No. 17/213,401, entitled "Pinch-To-Clamp Cannula Depth Limiter," filed on Mar. 26, 2021, published as U.S. Pub. No. 2021/0338273 on Nov. 4, 2021; U.S. patent application Ser. No. 17/213,409, entitled "Universal Size Multi-Walled Elastomer Cannula Depth Limiter," filed on Mar. 26, 2021, published as U.S. Pub. No. 2021/0338282 on Nov. 4, 2021; U.S. patent application Ser. No. 17/213,415, entitled "Threaded Cannula Depth Limiter," filed on Mar. 26, 2021, published as U.S. Pub. No. 2021/0338274 on Nov. 4, 2021; U.S. patent application Ser. No. 17/213,426, entitled "Tilting Tang Cannula Depth Limiter," filed on Mar. 26, 2021, published as U.S. Pub. No. 2021/0338283 on Nov. 4, 2021; U.S. patent application Ser. No. 17/213,431, entitled "Two Piece Separable Obturator," filed on Mar. 26, 2021, published as U.S. Pub. No. 2021/0338275 on Nov. 4, 2021; U.S. patent application Ser. No. 17/213,434, entitled "Latchless Obturator with Interference Fit Feature," filed on Mar. 26, 2021, published as U.S. Pub. No. 2021/0338269; U.S. patent application Ser. No. 17/213,508, entitled "Airflow Channels and Patterns in Lumen for Cannula," filed on Mar. 26, 2021, published as U.S. Pub No. 2021/0338278 on Nov. 4, 2021; and/or U.S. patent application Ser. No. 17/213,518, entitled "Stabilizer for Surgical Shafts or Cannulas," filed on Mar. 26, 2021, published as U.S. Pub. No. 2021/0338371 on Nov. 4, 2021. The disclosure of each of these patent applications is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, California. Similarly, those of ordinary skill in the art will recognize that various teachings herein may be readily combined with various teachings of any of the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 8,783,541, entitled "Robotically-Controlled Surgical End Effector System," issued Jul. 22, 2014, the disclosure of which is incorporated by reference herein; U.S. Pat. No. 8,479,969, entitled "Drive Interface for Operably Coupling a Manipulatable Surgical Tool to a Robot," issued Jul. 9, 2013; U.S. Pat. No. 8,800,838, entitled "Robotically-Controlled Cable-Based Surgical End Effectors," issued Aug. 12, 2014, the disclosure of which is incorporated by reference herein; and/or U.S. Pat. No. 8,573,465, entitled "Robotically-Controlled Surgical End Effector System with Rotary Actuated Closure Systems," issued Nov. 5, 2013, the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

I claim:

1. A surgical access device, comprising:
    (a) a cannula hub; and
    (b) a cannula tube connected to and extending distally from the cannula hub along a longitudinal axis, wherein the cannula tube is formed from a surgical steel that forms an inner surface defining a working channel configured to guide a surgical instrument along the longitudinal axis of the cannula tube, wherein the inner surface comprises a substantially constant inner diameter along an entire length of the cannula tube and is entirely unbroken along the entire length of the cannula tube, wherein the cannula tube comprises:
        (i) a tissue engagement feature disposed along an outer surface of the cannula tube, wherein the tissue engagement feature is configured to stabilize the cannula tube and the cannula hub relative to a body cavity wall of a patient when the cannula tube is inserted distally through the body cavity wall,
        (ii) a proximal portion of the cannula tube having a first wall thickness, wherein at least a portion of the proximal portion is disposed proximal to the tissue engagement feature, wherein at least a portion of the proximal portion of the cannula tube having the first wall thickness extends through and distally from the cannula hub, and
        (iii) a distal portion of the cannula tube having a second wall thickness, wherein the second wall thickness of the distal portion is greater than the first wall thickness of the proximal portion, wherein the second wall thickness extends for a greater length along the cannula tube than the first wall thickness.

2. The surgical access device of claim 1, wherein at least a portion of the distal portion is disposed distally relative to the tissue engagement feature.

3. The surgical access device of claim 2, wherein the distal portion of the cannula tube terminates into a pointed tip.

4. The surgical access device of claim 1, wherein the tissue engagement feature comprises a plurality of ribs.

5. The surgical access device of claim 4, wherein each rib of the plurality of ribs extends circumferentially along the outer surface of the cannula tube.

6. The surgical access device of claim 4, wherein each rib of the plurality of ribs comprises a shoulder and a distally presented tapered surface.

7. The surgical access device of claim 6, wherein the shoulder and the distally presented tapered surface of each rib of the plurality of ribs are coupled to each other at a rim.

8. The surgical access device of claim 1, wherein the cannula tube and the cannula hub are fixed relative to each other.

9. The surgical access device of claim 8, wherein the cannula tube and the cannula hub are fixed via a distally presented stem.

10. The surgical access device of claim 9, wherein the cannula tube and the cannula hub are welded together at the distally presented stem.

11. The surgical access device of claim 1, wherein the cannula hub is configured to selectively couple to a disposable seal housing.

12. The surgical access device of claim 1, wherein the tissue engagement feature extends laterally away from the longitudinal axis a further distance than a portion of the outer surface of the cannula tube at the proximal portion of the cannula tube.

13. The surgical access device of claim 1, wherein the cannula hub is formed from a surgical steel.

14. The surgical access device of claim 1, wherein the cannula hub is bell-shaped.

15. A surgical access device, comprising:
    (a) a cannula hub; and
    (b) a cannula tube connected to and extending distally from the cannula hub along a longitudinal axis, wherein the cannula tube is formed from a surgical steel that forms an inner surface defining a working channel configured to guide a surgical instrument along the longitudinal axis of the cannula tube, wherein the inner surface comprises a substantially constant inner diameter along an entire length of the cannula tube and is entirely unbroken along the entire length of the cannula tube, wherein the cannula tube comprises:
(i) a tissue engagement feature disposed along an outer surface of the cannula tube, wherein the tissue engagement feature is configured to stabilize the cannula tube and the cannula hub relative to a body cavity wall of a patient when the cannula tube is inserted distally through the body cavity wall,
(ii) a proximal portion of the cannula tube having a first wall thickness, wherein at least a portion of the proximal portion of the cannula tube having the first wall thickness extends through and is located distally relative to the cannula hub, and
(iii) a distal portion of the cannula tube having a second wall thickness, wherein the tissue engagement feature is interposed between the proximal portion and the distal portion, wherein the second wall thickness of the distal portion is greater than the first wall thickness of the proximal portion and the second wall thickness extends for a greater length along the cannula tube than the first wall thickness.

16. The surgical access device of claim 15, wherein the tissue engagement feature comprises a plurality of ribs arranged as a linear array.

17. The surgical access device of claim 16, wherein at least two ribs of the plurality of ribs are uniform in geometry.

18. The surgical access device of claim 15, wherein the cannula hub is formed from a sterilizable and reusable material.

19. A surgical access device, comprising:
(a) a proximal hub configured to selectively couple with a reusable seal housing; and
(b) a cannula tube connected to and extending distally from the proximal hub along a longitudinal axis, wherein the cannula tube is formed from a surgical steel that forms an inner surface defining an elongated channel configured to guide a surgical instrument along the longitudinal axis of the cannula tube, wherein the inner surface comprises a substantially constant inner diameter along an entire length of the cannula tube and is entirely unbroken along the entire length of the cannula tube, wherein the cannula tube comprises:
(i) a tissue engagement feature disposed along an outer surface of the cannula tube, wherein the tissue engagement feature is configured to stabilize the cannula tube and the proximal hub relative to a body cavity wall of a patient when the cannula tube is inserted distally through the body cavity wall,
(ii) a first cannula tube portion of the cannula tube having a first wall thickness, wherein at least a portion of the first cannula tube portion having the first wall thickness extends through and is located distally relative to the proximal hub, and
(iii) a second cannula tube portion of the cannula tube having a second wall thickness, wherein the second cannula tube portion terminates into a distal tip, wherein the tissue engagement feature is interposed between the first cannula tube portion and the second cannula tube portion, wherein the second wall thickness of the second cannula tube portion is greater than the first wall thickness of the first cannula tube portion, wherein the second cannula tube portion extends for a greater length along the cannula tube than the first cannula tube portion.

* * * * *